US012642594B2

(12) United States Patent
Mercer et al.

(10) Patent No.: US 12,642,594 B2
(45) Date of Patent: Jun. 2, 2026

(54) SYSTEMS AND METHODS FOR COUPLING NAVIGATION MARKERS TO AN ARRAY

(71) Applicant: DePuy Synthes Products, Inc., Raynham, MA (US)

(72) Inventors: Alasdair Mercer, Leeds (GB); Andrew Bailey, Leeds (GB)

(73) Assignee: DePuy Synthes Products, Inc., Raynham, MA (US)

( * ) Notice: Subject to any disclaimer, the term of this patent is extended or adjusted under 35 U.S.C. 154(b) by 793 days.

(21) Appl. No.: 17/338,365

(22) Filed: Jun. 3, 2021

(65) Prior Publication Data

US 2022/0387113 A1     Dec. 8, 2022

(51) Int. Cl.
| | |
|---|---|
| *A61B 34/20* | (2016.01) |
| *A61B 34/30* | (2016.01) |
| *A61B 90/00* | (2016.01) |

(52) U.S. Cl.
CPC .............. *A61B 34/20* (2016.02); *A61B 34/30* (2016.02); *A61B 2034/2072* (2016.02); *A61B 2090/3983* (2016.02)

(58) Field of Classification Search
CPC . A61B 34/20; A61B 34/30; A61B 2034/2072; A61B 2090/3983; A61B 90/39; A61B 2017/00477; A61B 2034/2055
See application file for complete search history.

(56) References Cited

U.S. PATENT DOCUMENTS

| | | | | |
|---|---|---|---|---|
| 6,096,048 | A * | 8/2000 | Howard, III | A61B 90/10 600/417 |
| 6,190,395 | B1 * | 2/2001 | Williams | A61B 34/20 606/130 |
| 10,792,109 | B2 | 10/2020 | Bonny et al. | |
| 2004/0167393 | A1 * | 8/2004 | Solar | A61B 90/39 600/414 |
| 2016/0331479 | A1 * | 11/2016 | Crawford | A61B 90/96 |
| 2019/0216454 | A1 * | 7/2019 | Thommen | A61B 90/57 |

FOREIGN PATENT DOCUMENTS

| | | | | |
|---|---|---|---|---|
| CA | 3021957 A1 * | 11/2016 | ............ | A61B 90/10 |
| EP | 0739182 B1 | 3/2006 | | |
| WO | 2021/059253 A2 | 4/2021 | | |

* cited by examiner

*Primary Examiner* — Pascal M Bui Pho
*Assistant Examiner* — Taylor Deutsch
(74) *Attorney, Agent, or Firm* — Condo Roccia Koptiw LLP

(57) ABSTRACT
A coupling system for securing and positioning a reflective marker in a navigation array is disclosed. The coupling system can include a carrier configured to hold the marker with a reflective element for detection by a surgical tracking system in a socket of the array. The carrier can include a body with an exterior for interfacing with the socket and an open end with engagement features for holding a body of the marker. The carrier is configured to visibly present the reflective element of the marker in the socket when the carrier is disposed in the socket. The carrier can be configured to securely hold the marker to the array when the marker is disposed in the carrier and the carrier is disposed in the array such that the marker cannot be removed from the carrier unless the carrier is removed from the socket.

20 Claims, 23 Drawing Sheets

11
GLOBAL AND BASE
COORDINATES

12
END EFFECTOR
COORDINATES

530

539

340

520

341

520

530

630

620

630

340

341

620

630

341

730

736   731   737

720

340

930

340

930

902

1030

1002

340

1204

1230

1202

340

1230

1202

1306

1304

1302

1308

1330

1402

1430

1604

1606

1602

SYSTEMS AND METHODS FOR COUPLING NAVIGATION MARKERS TO AN ARRAY

FIELD

This disclosure relates generally to surgical instruments, systems, and methods, and more particularly to devices, systems, and methods for coupling or integrating navigation markers into an array for subsequent use in locating a tool and/or a surgical robot during a surgical procedure. Navigational arrays comprising reflective markers disposed in a chassis and related methods for coupling the reflective markers to the chassis are disclosed herein, e.g., for locating, tracking, and/or navigating an instrument carrying the navigational arrays in association with, for example, a robotic or robot-assisted surgery.

BACKGROUND

Many different surgical procedures utilize some form of surgical navigation or tracking to aid in positioning surgical instruments relative to portions of patient anatomy during a procedure. One such type of procedure is robotic or robot-assisted surgical procedures, where surgical navigation can be important to correctly position a robotically controlled or assisted surgical instrument relative to a patient.

There are a number of known surgical navigation or tracking technologies, including commonly employed optical navigation or tracking systems that utilize, e.g., stereo-scopic sensors to detect infra-red (IR) light reflected or emitted from one or more optical markers affixed to surgical instruments and/or portions of a patient's anatomy. By way of further example, a tracker having a unique constellation or geometric arrangement of reflective elements can be coupled to a surgical instrument and, once detected by stereoscopic sensors, the relative arrangement of the elements in the sensors' field of view, in combination with the known geometric arrangement of the elements, can allow the system to determine a three-dimensional position and orientation of the tracker and, as a result, the instrument or anatomy to which the tracker is coupled.

In known surgical navigation technologies, a navigation array or tracker can be mounted on an instrument that is received and/or controlled by a robotic arm to identify a position of the instrument. In some instances, a navigation array or tracker can be formed integrally with the instrument itself. In other instances, a navigation array can be removably attached to an instrument and can be used to track a position of multiple instruments over the course of a surgical procedure. This approach, however, requires unmounting and remounting of the array with respect to each particular instrument every time a different instrument is used. Both solutions, however, can be inconvenient, as the capability to decouple the array from the instrument or to couple the array to other instruments may be absent or complicated. Further, many types of reflective markers that are used with navigation arrays are fragile and therefore are intended to be single-use devices, and arrangements having the reflective markers integrally-formed in a frame of the array can require the entire navigation array or instrument-array assembly to be single-use, or necessitate the replacement of the entire navigation array or instrument-array assembly if a reflective element is damaged during the operation. This has discouraged the use of robust and reusable navigation array that can provide a higher level of accuracy in positioning the reflective markers. Moreover, existing techniques for coupling single-use reflective markers to a navigation array chassis fail to accuracy locate the reflective marker in the chassis and result in an overall degradation of tracking accuracy.

Accordingly, there is a need for improved systems, methods, and devices for accurately coupling single-use reflective markers into a chassis, which can be a reusable chassis, a single-use chassis, or a chassis integrated with a surgical instrument.

SUMMARY

Disclosed herein are improved systems and methods for coupling navigation markers to navigation arrays that can then be utilized in any of a variety of procedures requiring surgical navigation of one or more instruments and/or portions of patient anatomy. The disclosed systems and methods for coupling the navigation markers can include a carrier housing configured to accept a reflective navigation marker, and the carrier housing can be accurately and robustly secured to a socket in a navigation array, and the navigation array can then be coupled to instruments and surgical robots during a surgical procedure to provide a precise location of the instrument or surgical robot when the reflective navigation markers are observed or otherwise detected by a surgical navigation system. Further, the disclosed systems and methods for coupling navigation markers to navigation arrays can include a variety of different coupling arrangements to aid in positioning the navigation marker in the navigation arrays in an optimum orientation and accurate position that allows for detection by a surgical navigation system (e.g., visual detection by one or more cameras included in a surgical navigation system). The systems, devices, and methods disclosed herein can find particular utility in allowing single-use reflective markers to be easily coupled to a reusable navigation array chassis in a manner that positions the reflective markers accurately and precisely to promote optimum performance of a surgical navigation tracking system.

Certain aspects of the present disclosure provide a coupling system for securing and positioning a navigation marker in a navigation array. The coupling system can include a navigation marker and a carrier housing. The navigation marker can include a body having proximal end having a navigation element configured to be precisely located by an optical tracking system, with the body defining a peripheral surface, and the carrier housing can include a body configured to be disposed in a navigation array. The body can define an open proximal end, an interior surface defining an interior void extending from the open proximal end, and an exterior surface configured to interface with a navigation array to couple the carrier housing to the navigation array. The carrier housing can be configured to secure and retain the navigation marker in the interior void such that the navigation element is presented at the open proximal end. In some embodiments, the carrier housing can be configured to secure and retain the navigation marker to the navigation array when the navigation marker is disposed in the carrier housing and the carrier housing is disposed in the navigation array. The peripheral surface of the navigation marker can be circular, and the body of the carrier housing can define an open cylindrical section.

In some embodiments, the interior surface of the carrier housing can include an interface configured to secure the navigation marker to the carrier housing.

Further, in some embodiments the interior surface of the carrier housing can be sized and shaped to create an interference fit with the peripheral surface of the navigation marker.

In some embodiments, the interior surface of the carrier housing can define a plurality of positioning elements sized and shaped to interface with the peripheral surface of the navigation marker to control the depth of the navigation marker in the interior void and align an axis of the navigation marker or navigation element with an axis of the carrier housing.

In certain embodiments, the interior surface of the carrier housing can define a stepped surface sized and be shaped to interface with a corresponding stepped section of the peripheral surface of the navigation marker to control the depth of the navigation marker in the interior void and align an axis of the navigation marker or navigation element with an axis of the carrier housing. In some embodiments, the plurality of positioning elements can be configured to align a central axis of the navigation marker with a central axis of the body of the carrier housing. In some embodiments, the plurality of positioning elements can be configured to align a central axis of the navigation marker with a central axis of the body of the carrier housing.

The body of the carrier housing can include a plurality of arms extending proximally to the proximal open end, the plurality of arms can include an inner surface defining at least a portion of the interior void and an outer surface defining at least a portion of the exterior surface of the body. In some embodiments, the outer surface of the plurality of arms can define a tapered profile when the navigation marker is disposed in the interior void, the tapered profile being shaped to interface with a corresponding surface of an opening of the navigation array and create an interference fit between the carrier housing and the navigation array. In some embodiments, each of the plurality of arms can define an angle of twist about a longitudinal axis. Each of the plurality of arms can define a curved inner surface and a curved outer surface each extending from a first end inner end to a second outer end of the arm, the inner end being closer to a central axis of the carrier housing, with each of the plurality of arms being configured to contact the navigation marker at a location along the inner surface closer to the inner end than the outer end. In some embodiments, each of the plurality of arms can be sized and shaped to be deflected about the longitudinal axis in a direction to reduce the angle of twist by the peripheral surface of the navigation marker. Additionally, each of the plurality of arms can be sized and shaped to be deflected about the longitudinal axis in a direction to reduce the angle of twist by an inner surface of a recess in the navigation array. In some embodiments, the deflection of each of the plurality of arms by the navigation marker generate a frictional force that retains the navigation marker in the carrier housing.

In certain embodiments, the exterior surface of the body of the carrier housing can include threaded features for threading the carrier housing into corresponding threaded feature of the navigation array. In some embodiments, the carrier housing can be configured to center the navigation marker in a circular opening of the navigation array. In some embodiments, the exterior surface can define an angled section at the open proximal end, the angled section being angled towards a central axis of the body and configured to be engaged by an inwardly extending lip of an opening of the navigation array in which the carrier housing is disposed, the engagement of the lip with the angled surface retaining the carrier housing in the opening of the navigation array.

Any of the features or variations described above can be applied to any particular aspect or embodiment of the present disclosure in a number of different combinations.

The absence of explicit recitation of any particular combination is due solely to the avoidance of repetition in this summary.

BRIEF DESCRIPTION OF DRAWINGS

This disclosure will be more fully understood from the following detailed description taken in conjunction with the accompanying drawings, in which.

DETAILED DESCRIPTION

Figure 1:
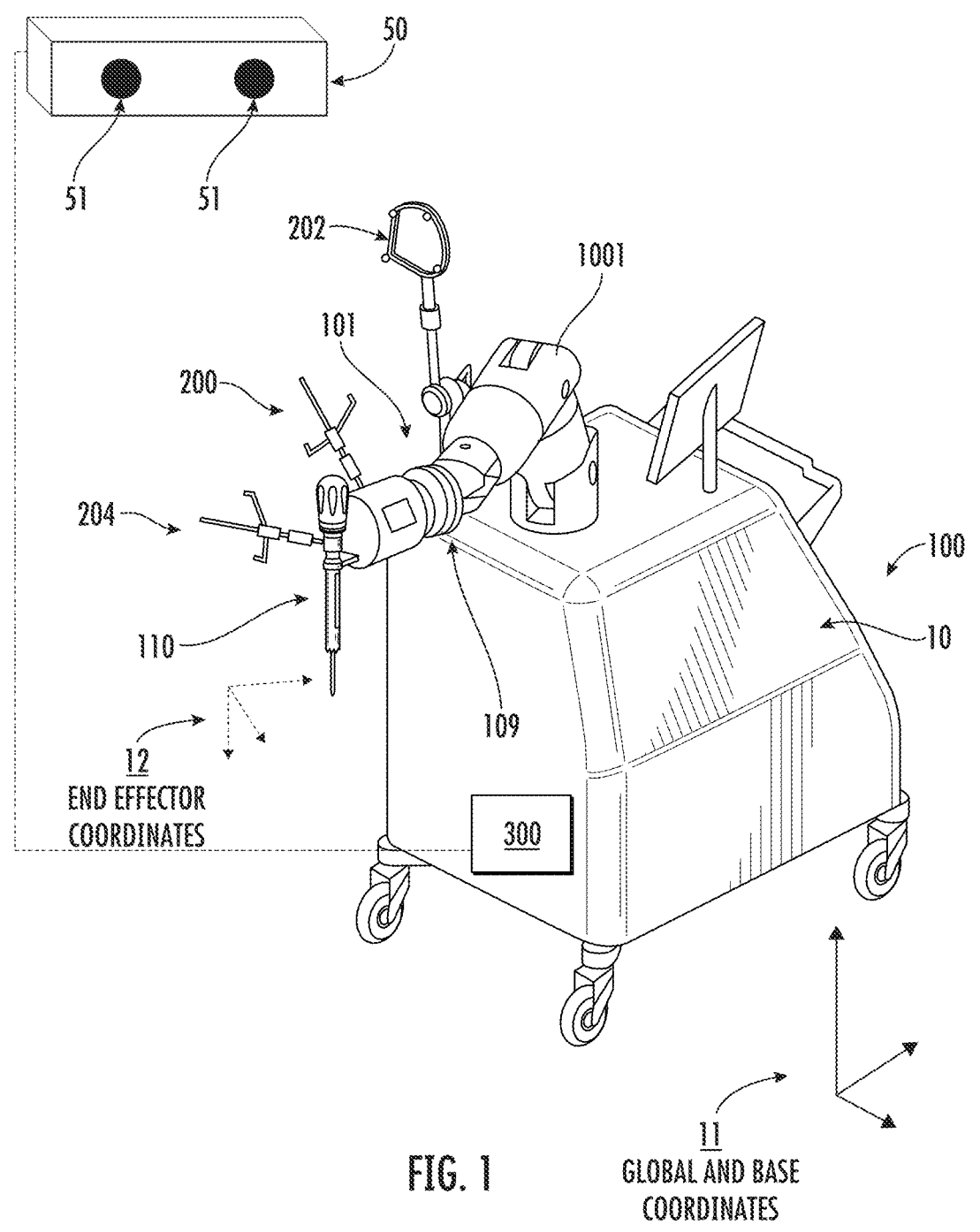
FIG. 1 is a schematic of a surgical robot with an attached end effector and a surgical navigation marker array disposed on the surgical robot for use in tracking the position of the distal end of the surgical robot and end effector.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices and methods specifically described herein and illustrated in the accompanying drawings are non-limiting example embodiments and that the scope of the present disclosure is defined solely by the claims. The features illustrated or described in connection with one embodiment may be combined with the features of other embodiments. Such modifications and variations are intended to be included within the scope of the present disclosure.

Additionally, to the extent that linear or circular dimensions are used in the description of the disclosed devices, systems, and methods, such dimensions are not intended to limit the types of shapes that can be used in conjunction with such systems and methods. Equivalents to such linear and circular dimensions can be determined for any geometric shape. Further, in the present disclosure, like-numbered components of the embodiments generally have similar features. Still further, sizes and shapes of instruments or systems, and the components thereof, can depend at least on the anatomy of a subject with which the instruments or systems will be used, the size and shape of other components with which the instruments or systems will be used, and the methods and procedures in which the instruments or systems will be used.

Devices, systems, and methods for coupling navigation markers to surgical navigation arrays are disclosed herein, e.g., a carrier housing for retaining and precisely locating a single-use reflective navigation marker in the carrier housing with the carrier housing itself being configured to be disposed in a socket of a frame of a navigation array such that the reflective navigation maker is precisely positioned in the socket. In some embodiments, a carrier housing of the present disclosure can include a plurality of arms extending proximally to form an open proximal end of the carrier housing, the open proximal end being sized and shaped to receive the body of single-use navigation marker and retain the single-use navigation marker in the open proximal end of the carrier housing. Additionally, the arms can include one or more exterior features for securing the carrier housing in a socket of a frame of a navigation array. In some embodiments, the arms concentrically place a center of the navigation marker in a center of the socket of the frame, with the arms being flexible to account for variances in the size and shape of the reflective marker. In some embodiments, the carrier housing includes a threaded exterior, for example at a distal end thereof opposite the open proximal end, for being threaded into a corresponding set of threads on the inner surface of the socket of the frame of the navigation array. Aspects of the present disclosure provide systems and methods for accurately and easily coupling single-use navigation markers, which are often delicate with minimal engagement features, into a wide variety of navigation arrays by way of a carrier housing configured to securely retain the navigation marker and provide a more robust coupling mechanism for use with a socket of a navigation array. In some embodiments, a carrier housing of the present disclosure can include a plurality of twisted arms, each being configured to have a first inner end that is configured to engage with an exterior periphery of a body of the navigation marker and a second outer end that is configured to engage with an inner surface of a socket of a frame of a navigation array such that engagement of the carrier housing and navigation marker with the socket reduces the degree of twist of each arm and concentrically places the navigation marker in the center of the socket of the frame. In some embodiments, the navigation marker can be a reflective marker that includes a lens element and a reflective element visible through the lens element, e.g., a hemispherical or spherical clear lens with a reflective surface or reflective element configured to be visible through the lens element.

In operation, the navigation array with the carrier housing and navigation markers disposed therein can be coupled to a surgical robotic arm, other instrument, or other component, and can be configured to locate an absolute position of the robotic arm or other component in three-dimensional space, such as the distal end of the robotic arm where a tool end effector is present. For example, a navigation array can be mounted on the tool end effector (e.g., directly onto a tool carried by a tool holder or on the tool holder) and can be configured to locate a position of the tool end effector based on a position of the array. In this manner, the array can precisely track a spatial parameter, such as distance, depth, or orientation, of a distal end of the tool end effector without any additional sensors or encoders present on the robotic arm. As such, a need to provide electronics in each instrument or instrument mount used throughout a surgical procedure can be eliminated. Accordingly, the navigation arrays of the present disclosure can locate absolute placement of the robotic arm and associated instrumentation during a surgical procedure in an effective and efficient manner without disrupting surgical flow or requiring excessive handling of instrumentation.

FIG. 1 illustrates embodiments of computer-assisted surgical (CAS) systems that can be utilized with the systems and methods described herein. Such systems can utilize any of surgical navigation/tracking and robot control or assistance to monitor or control movement of one or more surgical instruments during a procedure. While the illustrated embodiments and accompanying description do not make particular reference to a specific surgery, the systems and methods described herein can be utilized in various applications involving robotic, robot-assisted, and non-robotic operations where computer-assisted tool location are required, and precise adjustment of tool position may be appropriate. Example applications include knee surgery, e.g., total knee arthroplasty (TKA) or unicompartmental knee arthroplasty (UKA), hip surgery, e.g., hip arthroplasty, shoulder surgery, spine surgery, etc. The teachings of the present disclosure can be applied to such procedures; however, the systems and methods described herein are not limited to these applications.

FIG. 1 shows an overview of a surgical system according to the present disclosure. In FIG. 1 a robotic device 100, including a surgical robot arm 1001, that includes an attached tool end effector 110 and a plurality of arm segments 101 connected by rotatable or otherwise articulating joints 109. A distal-most segment can include a navigation array 200 mounted thereto and terminates at distal end with the tool end effector 110. FIG. 1 also shows a global coordinate system 11 of the robotic device 100 and an end effector coordinate system 12 of the tool end effector. The global coordinate system 12 can be defined in different ways and, in some embodiments, can use the location of a base 10 of the robotic device 100, which may or may not itself be stationary, as an origin. The location of the distal-most arm segment of the robotic device can be calculated by receiving a position signal from an encoder in each joint 109 and/or by measuring a position of the navigation array 200 to directly detect the position of the arm segment and determine the position of the distal end thereof in the global coordinate system 11. In some instances, a measured coordinate system of the navigation array 200 can be different from the global coordinate system 11 and calculations can be utilized to harmonize the two coordinate systems. In some embodiments, the measured coordinate system can be used as the global coordinate system 11. The end effector coordinate system 12 can be defined in different ways, but can refer to the position and orientation of the tool end effector 110 with respect to the operation of the tool end effector (e.g., if the tool end effector includes a cutting bit, the cutting direction can be along an "up" or "down" axis that might be defined by, e.g., a longitudinal axis of the tool). The tool end effector 110 held by the robotic device 100 can be constrained to move about the distal end of the distal-most arm segment such that the summation of the positions of joints 109 can define the location of the end effector coordinate system 12 in the global coordinate system 11 with respect to a control system of the joints 109 to control movement of the tool end effector 110. Accordingly, the robotic device 100 can be connected to a control unit 300 that controls the actuation of each joint 109 in order to position the tool end effector 110. The control unit 300 typically comprises power supply, AC/DC converters, motion controllers, and other components to power the motors of the actuation units in each joint 109, as well as fuses, real-time control system interface circuits, and other components conventionally included in surgical robot devices. As noted above, the description provided herein makes reference to the surgical system shown in FIG. 1, but the present disclosure is also contemplated for use with any surgical device, for example, a saw blade, burr, reamer, mill, knife, or any other implement that could cut or deform bone and is appropriate for use in a given operation. Further, the present disclosure is also contemplated to include use of such instruments by surgical robots, by users with some degree of robotic assistance, and without involvement of surgical robots or robotic assistance (e.g., where solely surgical navigation/tracking is utilized).

Further, in some embodiments additional and/or alternative navigation arrays can be employed in addition to, or in place of, the navigation array 200 shown attached to a distal-most arm segment 101 of the robotic arm 1001. For example, in some embodiments a navigation array 202 can be coupled to another component of the robotic device, such as a base of the robotic arm 1001 in embodiments where the robot is mobile. Still further, a navigation array 204 can be coupled to the tool end effector itself. In embodiments where a single tool is provided, the array 204 can be coupled directly thereto. In other embodiments, however, the tool end effector 110 can be a cannula or guide configured to receive one or more surgical instruments. In such embodiments, the navigation array 204 can be coupled to the cannula or guide and positioning of an instrument inserted therethrough can be achieved using a different array or different tracking means.

Returning to the system illustrated in FIG. 1, the system also comprises a tracking unit 50, such that the relative pose or three-dimensional position and orientation of the navigation array 200 (and/or other navigation arrays) can be tracked in real time and shared to the control unit 300 and any additional planning or control system. In some instances, coordinate systems can be attached to the robotic device 100 via the navigation array 200, the end effector 110 via a tool array (e.g., array 204), and an anatomical structure (not shown). The tracking unit 50 can measure the relative motions between any and all coordinate systems in real time. Real time can, in some embodiments, mean high frequencies greater than twenty Hertz, in some embodiments in the range of one hundred to five hundred Hertz, with low latency, in some embodiments less than five milliseconds.

Figures 2A, 2B:
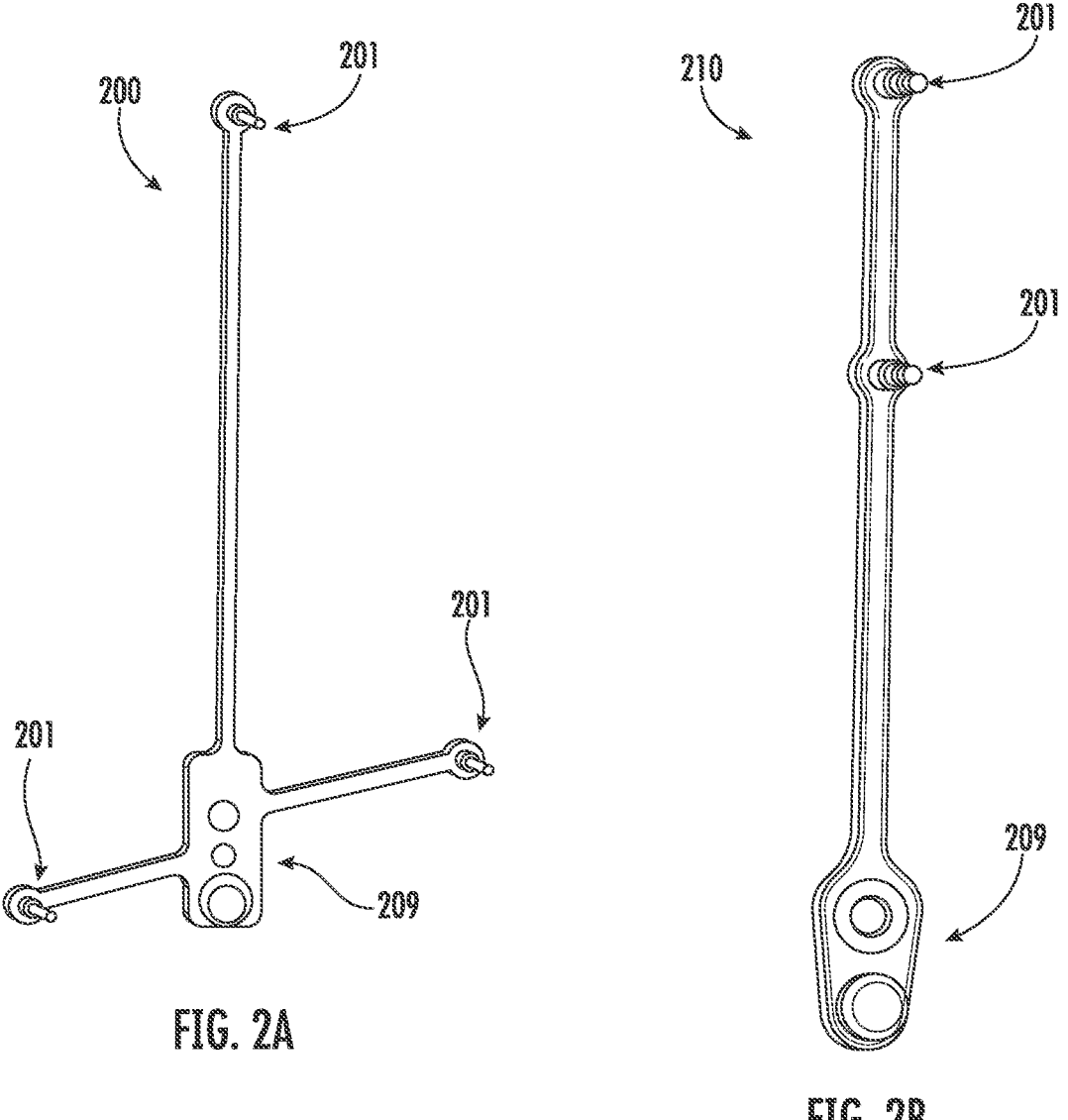
FIG. 2A is a perspective-view illustration of an example surgical navigation array having three markers and configured to locate an attachment point in three-dimensional space by a navigation system.
FIG. 2B is a perspective-view illustration of a navigation arraying having two markers and configured to locate axis of an attachment point in three-dimensional space.

FIGS. 2A and 2B show example conventional navigation arrays that can be used with the tracking unit 50. FIG. 2A is an illustration of a navigation array 200 having three markers and configured locate an attachment point in three-dimensional space by a navigation system. FIG. 2B is an illustration of a navigation array 210 having two markers and configured to locate an axis of an attachment point in three-dimensional space. The navigation arrays 200, 210 can utilize any of a variety of trackers and tracking technologies known for use in surgical navigation. These can include, for example, optical trackers consisting of reflective or active markers detected by a sensor 51 (shown as part of the tracking unit 50 in FIG. 1) disposed inside or in view of the surgical field. In the illustrated embodiments, for example, the tracking unit 50 can include a passive optical tracker consisting of, for example, a constellation of reflective tracking elements 201 having a fixed geometric relationship that can be coupled to a portion of patient anatomy, a surgical instrument, or other component to be tracked. The tracking unit 50 can include a stereoscopic sensor having two or more physically separated detectors 51 that can be used to detect light reflected off each of the tracking elements (e.g., reflected infra-red (IR) light in some embodiments). The sensor 51, in some embodiments in conjunction with other information processing components such as the control unit 300, can utilize the known fixed geometric relationship between the tracking elements 201, a mounting point 209, and the detected positions of the tracking elements in the fields of view of the two detectors 51 to determine a precise three-dimensional position and orientation of the navigation array 200, 210 (and therefore of the anatomy, tool, or robotic segment coupled via the mounting point 209) within the surgical field.

In some embodiments, however, other types of surgical navigation and tracking can be employed in place of, or in addition to, the above-described reflective optical tracking. For example, in some embodiments optical tracking can be employed using active light emitters rather than reflective elements, such as light emitting diodes (LEDs). In other embodiments, electromagnetic trackers can be employed, while in still other embodiments any of inertial sensors using gyroscopic measurements, ultrasonic sensors, radio-frequency identification (RFID) sensors, or other known sensors can be employed.

Regardless of how it is gathered, position and orientation data can be transferred between components (e.g., to the control unit 300) via any suitable connection, e.g., with wires or wirelessly using a low latency transfer protocol. The real-time control unit 300 can carry out real-time control algorithms at a reasonably high frequency with low additional latency to coordinate movement of the robotic device 100.

Prior navigation arrays like those shown in FIGS. 2A and 2B can have drawbacks, however. For example, when utilizing optical reflective markers as described above, manufacturers or users are required to couple the reflective markers to the plurality of tracking element posts 201. This can be done by adhesive, ultrasonic welding, interference fit, etc. The reflective markers, however, often have poor dimensional control on the feature, such as a recess, that is utilized to couple to the tracking element posts 201. For example, a recess formed on the reflective marker might be larger than the tracking element post 201, which can allow the reflective marker to move about the post and possibly be secured at a non-concentric location. As a result, there can be variation in reflective marker placement that can exceed tolerances needed for optimal navigation tracking (e.g., greater than about 0.05 mm or greater than about 0.1 mm in some embodiments). Further, in some embodiments the navigation arrays are coupled to surgical instruments that produce higher frequency vibrations as opposed to gross movement, e.g., oscillating saws, etc. Vibrations created by such an instrument can be transmitted via the rigid connection to the navigation array and optical reflective markers, and these vibrations can be significant enough that they interfere with performance of the navigation system (e.g., the ability of the tracking unit 50 to accurately determine the position of the reflective markers).

Figure 3:
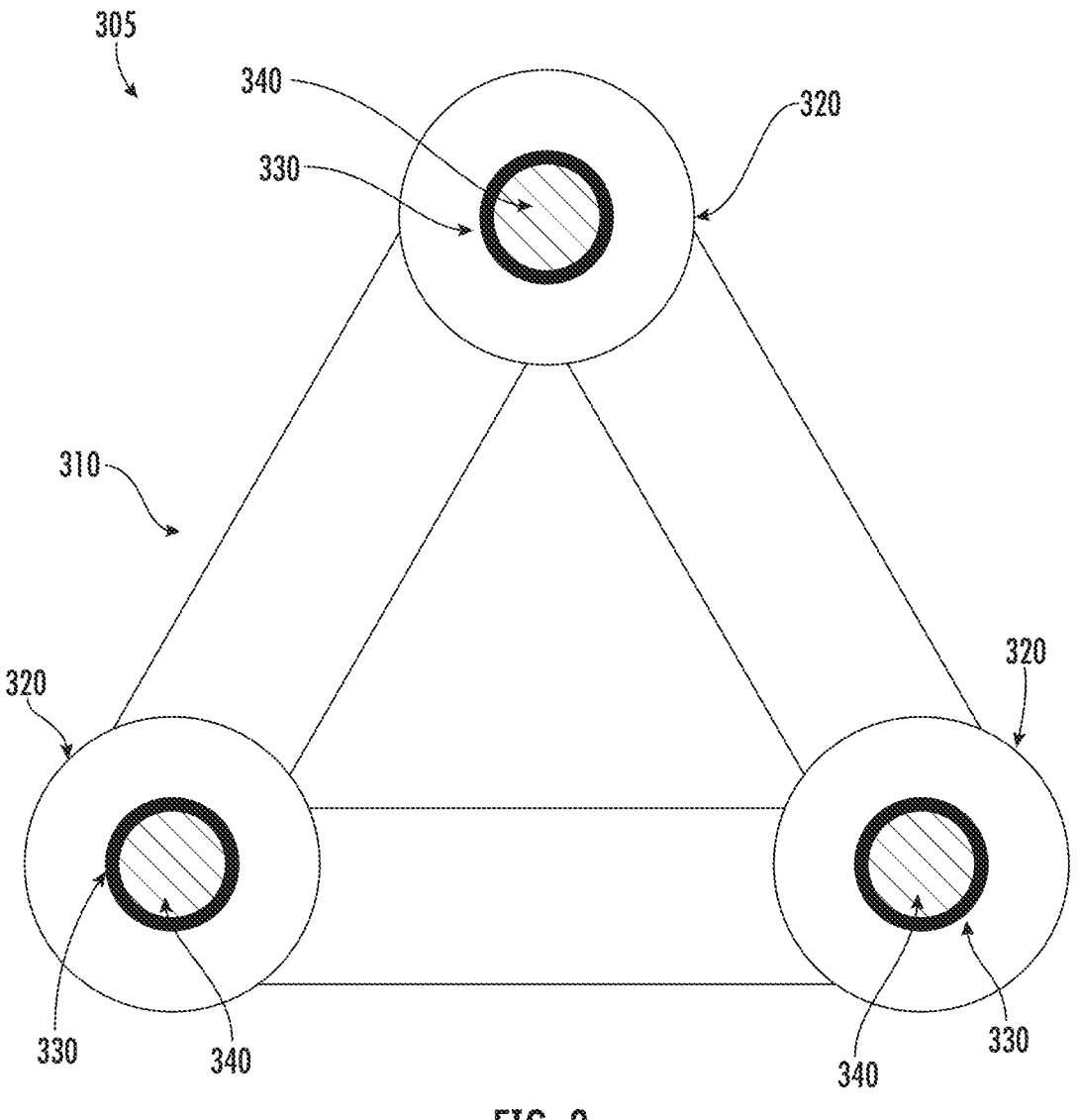
FIG. 3 is a top-view illustration of one embodiment of a navigation array having three single-use navigation markers disposed in a frame of the navigation array with a triangular configuration.

FIG. 3 is an illustration of one embodiment of a navigation array 305 according to the present disclosure that can utilize three single-use reflective navigation markers 340 disposed in a frame 310 of the navigation array with a triangular configuration. The triangular configuration and number of reflective navigation markers is merely an example. Embodiments according to the present disclosure can utilize any number of navigation markers, e.g., at least two to determine an axis in three-dimensional space and at least three to determine a position and orientation in three-dimensional space. In some embodiments, a greater number of reflective markers are utilized to provide higher fidelity tracking, e.g., five or six markers in some embodiments, and up to 20 or more in certain embodiments. Further, a number of arrays can be utilized in a surgical procedure to track the positions of several instruments simultaneously. In such embodiments, each array can have a unique geometrical configuration that places the number of reflective markers at unique distances relative to one another as compared to any other array in use.

The navigation array 305 includes three sockets 320, each connected by the frame 310, and each socket 320 includes a carrier housing 330 coupled thereto with each carrier housing 330 retaining one of the navigation markers 340 to the carrier housing 330 and, thereby, to the socket 320. The frame 310 and sockets 320 of the navigation array 305 can be single-use or reusable and made from a variety of materials, such as metal or a variety of polymers that can rigidly and accurately position the sockets 320 with respect to each other.

In operation, a navigation marker 340 and carrier housing 330 can be coupled together in advance of being assembled into the sockets 320 of the array 305. Each socket 320 can securely retain the carrier housing 320 in a variety of ways, examples of which are provided in more detail below. For example, the carrier housing 330 can be threaded into the socket 320. Additionally, the carrier housing 330 can retain the navigation marker 340 in a variety of different ways such that a center of reference location of the navigation marker 340 is accurately and/or concentrically located within the socket 320 in order to maintain an overall precision of the calculated location of the array 305 as determined by observation of the navigation markers 340 in combination with a known spatial relationship between the sockets 320.

Such navigation arrays can offer several advantages. For example, the carrier housing 330 can be configured to retain the navigation marker 340 in a manner that is self-centering and, in some embodiments, does not rely on a post/recess interaction where poor dimensional tolerance can allow for off-center mounting of a navigation marker. Further, the carrier housing 330 can be integrated into the sockets of the navigation array frame 310 in a manner that is similarly self-assembling and self-centering, thereby ensuring accurate and precise positioning of the reflective marker 340 relative to the frame 310. Further, the components can provide for easy assembly by a manufacturer or user either before or during a surgical procedure. For example, in some embodiments the reflective markers 340 and carrier housings 330 can be provided assembled together and a user can quickly couple the reflective marker/carrier housing assembly to the navigation array frame 310 when preparing the frame for use in a procedure. In some embodiments, a dispenser could be provided in a surgical field or prep area that includes a plurality of assembled markers 340 and carrier housings 330, e.g., stacked in an elongate tube. A user can dispense a marker/housing assembly and assembly to a navigation array frame 310 as they prepare to couple the array to an instrument. Such a configuration can provide advantages for manufacturing and packaging a single type of reflective marker and carrier housing and allowing a user to employ these with a variety of individual navigation array frames.

Still further, in some embodiments the assembly of the navigation marker 340 and carrier housing 330 can be a single-use component, while the navigation array frame 310 can be a reusable component. Continuing the example above, a dispenser can be provided containing a number of new, sterile assemblies of a navigation marker 340 and carrier housing 330. A user can dispense a needed number of such assemblies and couple to the available sockets of one or more navigation array frames to be used in a surgical procedure. After the procedure is completed, the navigation marker and carrier housing assemblies can be separated from the navigation array frame and disposed of, while the navigation array frame can be cleaned and sterilized for use with new navigation marker and carrier housing assemblies in a future operation. In some embodiments, the navigation marker 340, carrier housing 330, and navigation array frame 310 can each be formed from various materials, including polymers and metals.

A further advantage provided by some embodiments disclosed herein is an ability to damp vibrations passed from a surgical instrument to the reflective markers of the navigation array. As will be apparent from the additional description below, embodiments that make use of balanced or symmetrically-arrayed movable, biased, and/or deformed elements can provide for self-centering of a navigation marker and an ability to dampen vibrations transmitted thereto. This can aid tracking performance by minimizing vibrations that might impair the tracking unit 50 from accurately determining a position of a navigation marker.

Figure 4A:
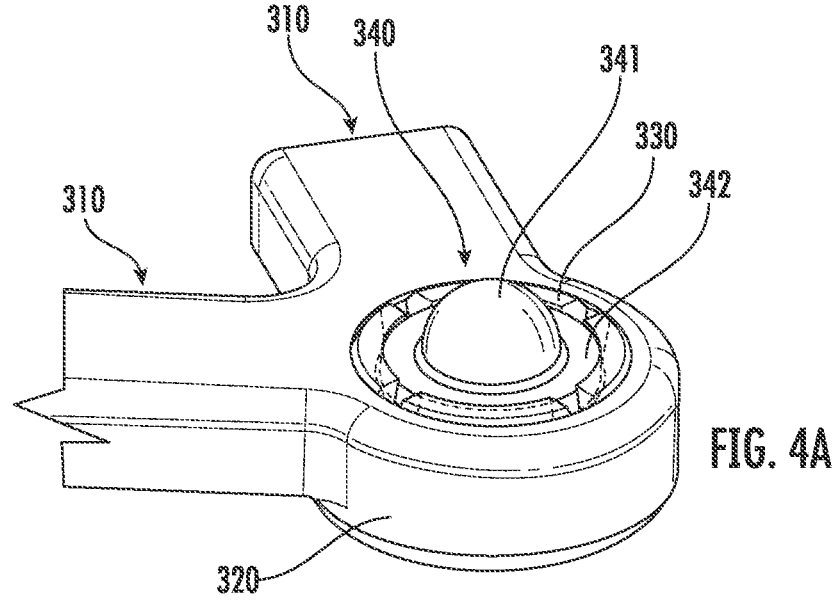
FIG. 4A is a perspective-view illustration of one navigation array embodiment showing a single-use navigation marker disposed in a carrier housing, with the carrier housing being disposed in a frame of the navigation array.

FIG. 4A is an illustration of a navigation array embodiment showing a single-use reflective navigation marker 340 disposed in a carrier housing 330, with the carrier housing 330 being disposed in a socket 320 of the navigation array 305. The navigation marker 340 is shown to include a hemispherical lens element 341 that can, for example, be a clear lens that visibly presents a view of a reflective surface disposed on an opposite of the lens. Reflective markers of this type include, for example, the NDI Radix™ Lens, which have a body with a hemispherical polycarbonate lens opposite a larger hemispherical element with a reflective surface that is visible through the hemispherical lens. As shown in more details in FIGS. 4B-4F, the carrier housing 330 includes a plurality of arms forming an opening in which the reflective marker 340 is disposed. Each arm can include an inner interface element configured to secure a peripheral flange 342 of the reflective marker 340. In some instances, when the carrier housing 330 is installed in the socket 320, the reflective marker 340 cannot be removed by way of the arms being unable to deflect due to their engagement with the wall of the socket 320, as shown in more detail in FIG. 4B.

Figure 4B:
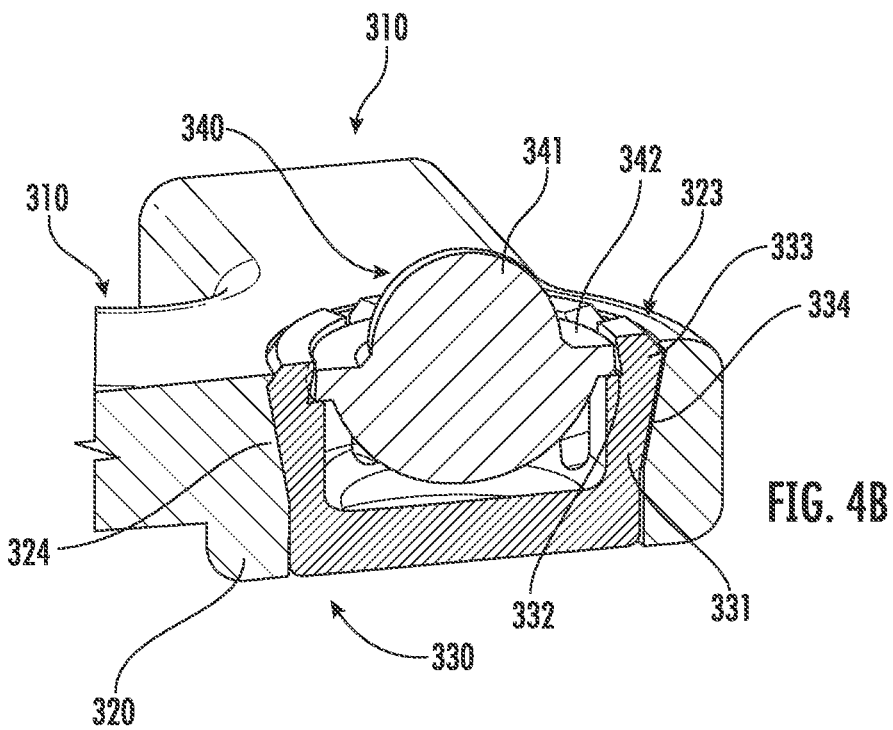
FIG. 4B is a perspective-cross-sectional view illustration of the embodiment of FIG. 4A, showing the coupling interaction between the a single-use navigation marker, the carrier housing, and the frame of the navigation array.

FIG. 4B is a cross-section illustration of the embodiment of FIG. 4A, showing the coupling interaction between the single-use navigation marker 340, the carrier housing 330, and the socket 320 of the navigation array 330. Each arm 331 of the carrier housing 330 includes an inner retaining feature 332 that is in engagement with the flange 342 of the navigation marker 340 to hold the navigation marker. Additionally, each arm 331 can include an outer retaining feature 333 that is configured interface with, for example, an inwardly protruding lip 323 of the socket to retain the carrier housing 330 in the socket 320. Each arm 331 also defines a tapering exterior surface 334 that is in contact with a tapering inner surface 324 of the socket, which can, for example, generate an interference fit between the carrier housing 330 and the socket 320.

Figure 4C:
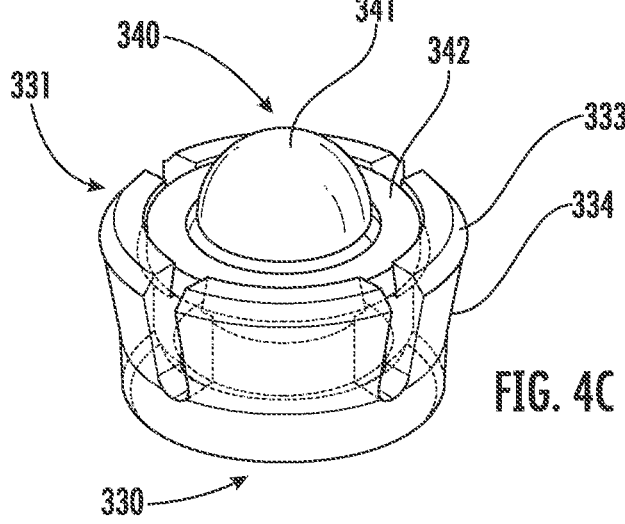
FIG. 4C is a perspective-view illustration of the single-use navigation marker and the carrier housing of FIG. 4A.
Figure 4D:
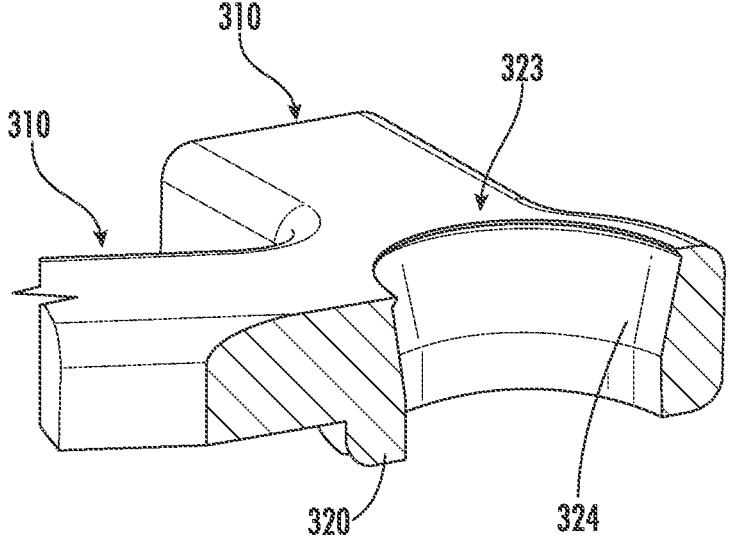
FIG. 4D is a perspective-cross-sectional view illustration of a coupling socket of the frame of the navigation array of FIG. 4A, with the coupling socket being configured to receive and secure the carrier housing to the frame.
Figure 4E:
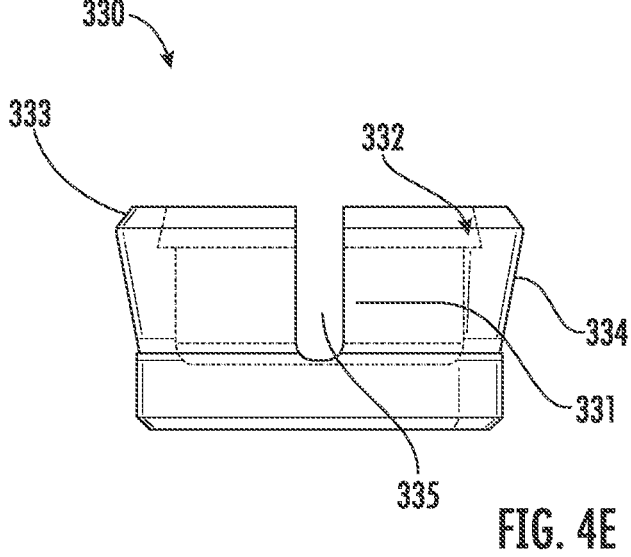
FIG. 4E is a side-view illustration of the carrier housing of FIG. 4A.
Figure 4F:
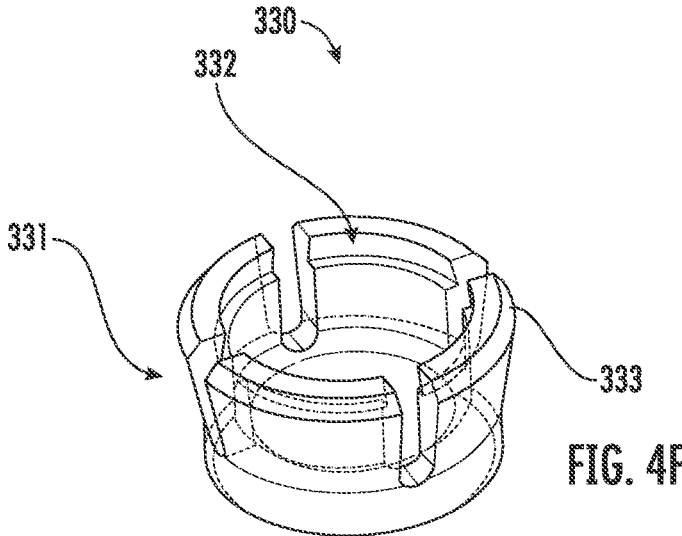
FIG. 4F is a partially-transparent perspective-view illustration of the carrier housing of FIG. 4A.

FIG. 4C is an illustration of the single-use navigation marker 340 and the carrier housing 330, showing the individual arms 331 in more detail, along with a bevel of the outer retaining feature 333. FIG. 4D is a cross-section illustration of a coupling socket 330 of the navigation array 305, with the coupling socket 320 being configured to receive and secure the carrier housing 330 to the frame with the tapered inner surface 324 and the inwardly protruding lip 323 formed in the proximal edge of the socket 320. The lip 323 can help to set a proper depth of insertion of the carrier housing 330 which, in turn, can help set a proper position of the navigation marker 340 relative to the frame 310 along the axis of the socket 320. In this manner, the carrier housing 330 and socket 320 interaction can accurately and precisely position the navigation marker 340 in X-, Y-, and Z-axes relative to the navigation array frame 310 to ensure the marker is in an expected location relative to the frame and optimize tracking performance. The lip 323 can also prevent the carrier housing 330 from popping out of the socket 320 proximally due to interaction with the bevel of the outer retaining feature 333. FIGS. 4E and 4F are illustrations of the carrier housing 330 embodiment of FIG. 4A, showing the space 335 defined by the plurality of arms 331 and an inwardly sloped surface of the inner retaining features 332 that is configured to prevent removal of the navigation marker 340 from the carrier housing 330 when the arms 331 are held in an inwardly-urged position by an interaction between the tapered exterior surface 334 of the carrier housing 330 and the tapered inner surface 324 of the socket. The arms 331 can be maintained in such a position by the outer retaining feature 333 once the carrier housing 330 passes distally beyond the inwardly protruding lip 323 of the socket 320.

Figures 5A, 5B:
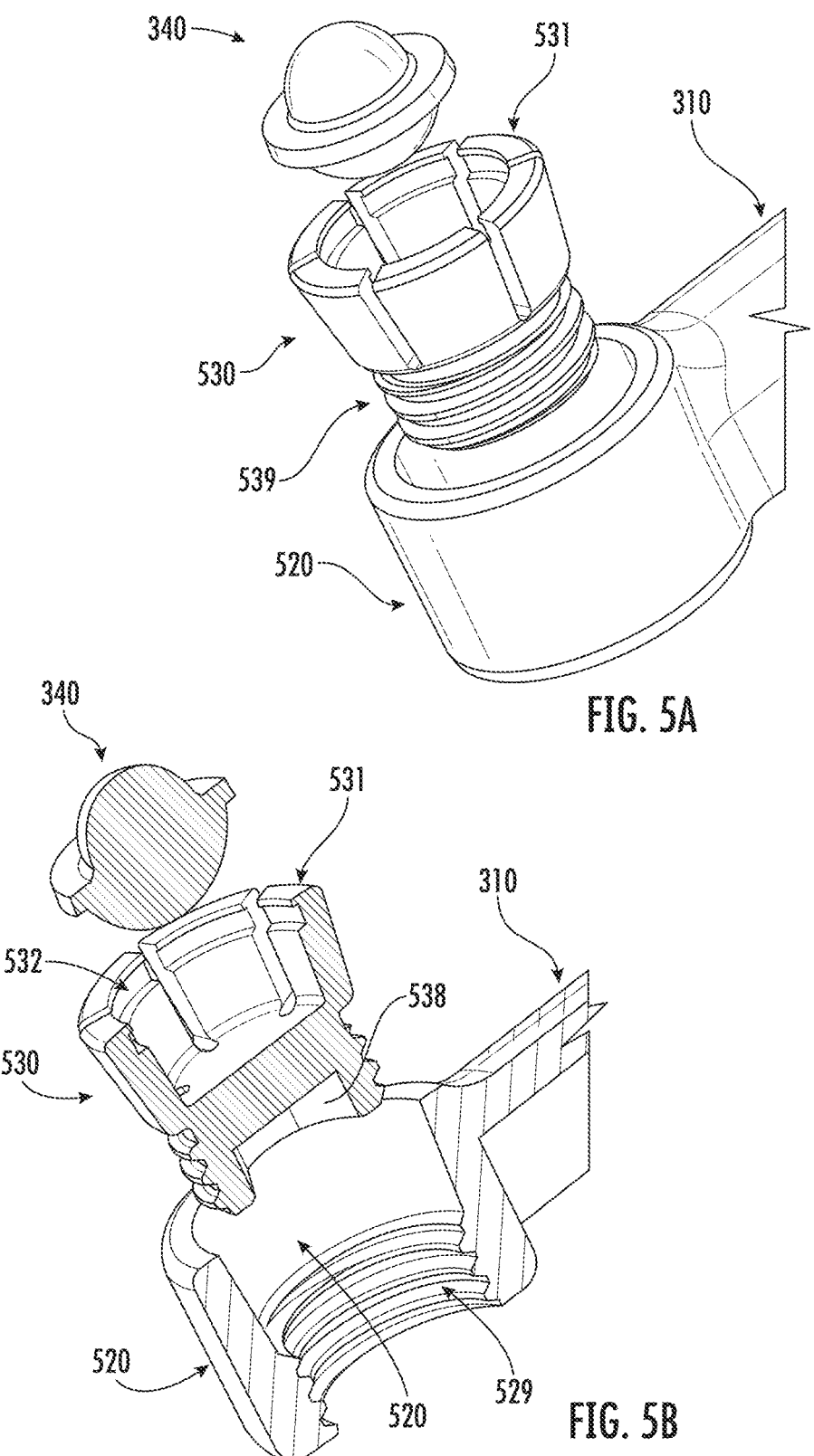
FIG. 5A is an exploded-view illustration of one embodiment of a carrier housing and navigation array coupling socket configured to retain and precisely locate a navigation marker in the coupling socket of the frame of the navigation array.
FIG. 5B is an exploded-cross-sectional view of the embodiment of FIG. 5A.

FIG. 5A is an exploded-view illustration of one embodiment of a carrier housing 530 and coupling socket 520 configured to retain and precisely locate a navigation marker 340 in the coupling socket 520 of the frame 310 of the navigation array 305. The carrier housing 530 includes a distal end with an external thread 539 that is configured to thread the carrier housing 530 into the socket 520, as shown in more detail in FIG. 5B. Returning to FIG. 5A, the carrier housing 530 includes a plurality of proximally extending arms 531 that define an opening to receive the navigation marker 340, with each arm 531 having an internal engagement feature, which is formed as a peripheral channel 532 to receive the peripheral flange 342 of the navigation marker 340.

FIG. 5B is a cross-sectional view of the embodiment of FIG. 5A and shows the inner threading 529 of the socket 520 that is configured to receive that external thread 539 of the carrier housing 530. Additionally, the distal end of the carrier housing 530 includes a hex or other form of socket 538 for engagement with a tool to rotate and thread the carrier housing 530 into and out of the socket 520.

Figure 5C:
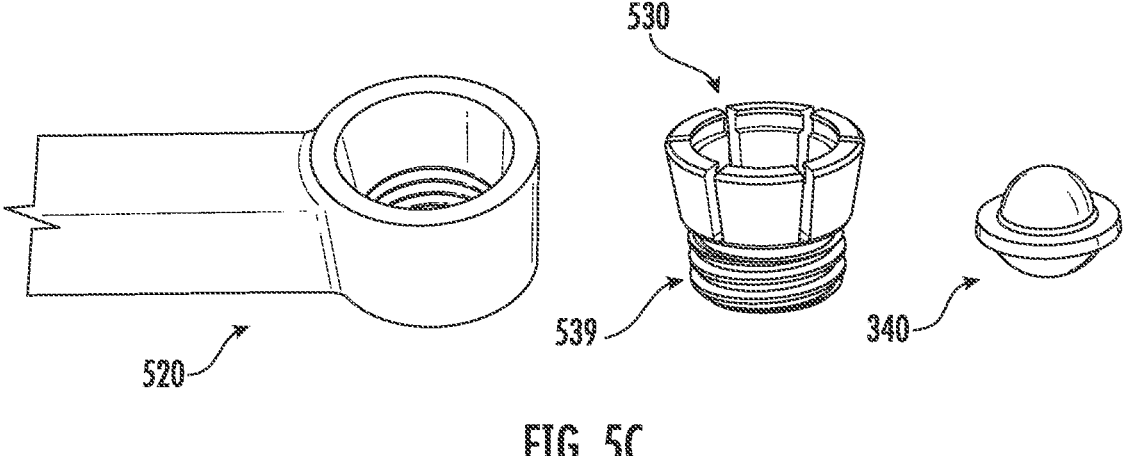
FIG. 5C is a perspective-view photograph of the components of the embodiment of FIG. 5A.
Figure 5D:
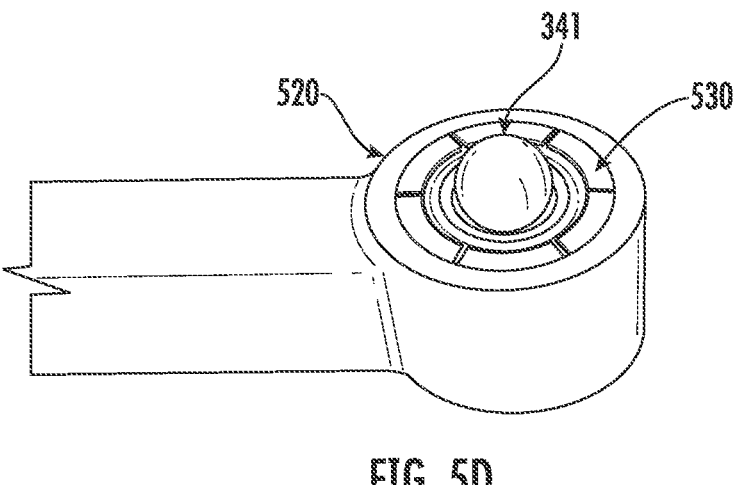
FIG. 5D is a perspective-view photograph of the components of FIG. 5C in an installed configuration.

FIG. 5C is a photograph of the components of the embodiment of FIG. 5A, showing the threaded socket 520, the carrier housing 530, with distal external threads 539 visible, and the loose navigation marker 340. FIG. 5D is a photograph of the components of FIG. 5C in an installed configuration, with the navigation marker 340 disposed in the carrier housing 530, with the arms 531 securing the peripheral flange 342 of the navigation marker 340, and with the carrier housing 532 threaded into the socket 520 of the array 305. In some embodiments, the arms 531 can be configured to prevent removal of the navigation marker 340 from the carrier housing 530 when the carrier housing 530 is threaded into the socket 520 due to the arms 531 being inwardly compressed into engagement with the peripheral flange 342 of the navigation marker 340 such that the peripheral channel 532 securely retains the navigation marker 340.

Figures 6A, 6B:
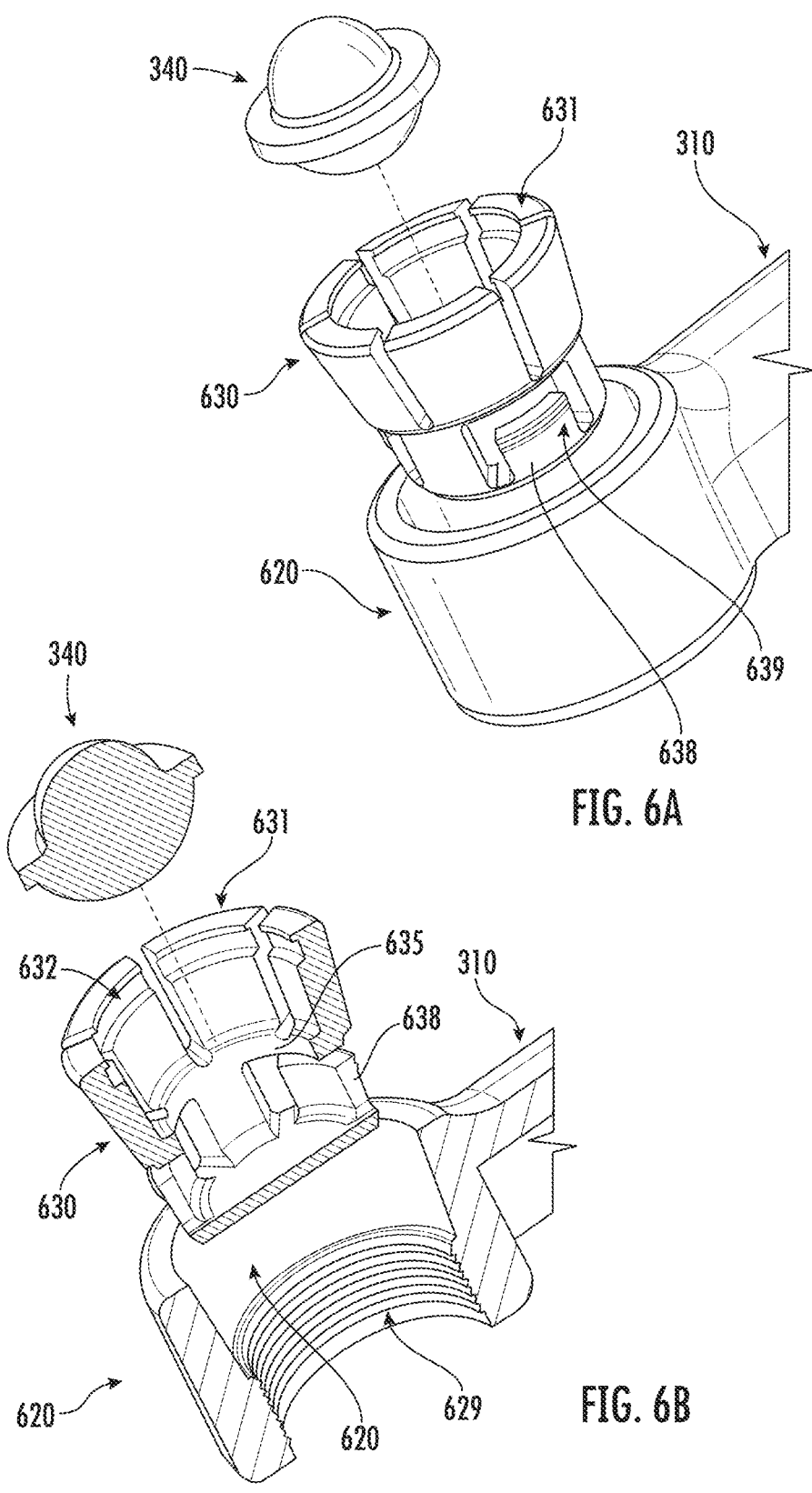
FIG. 6A is an exploded-view illustration of one embodiment of a carrier housing and navigation array coupling socket configured to retain and precisely locate a navigation marker in the coupling socket of the frame of the navigation array.
FIG. 6B is an exploded-cross-sectional view of the embodiment of FIG. 6A.

FIG. 6A is an exploded-view illustration of another embodiment of a carrier housing 630 and coupling socket 620 configured to retain and precisely locate a navigation marker in the coupling socket 620 of the frame of a navigation array 305. The carrier housing 630 includes a plurality of proximally extending arms 631 that define an opening to receive the navigation marker 340, with each arm 631 having an internal engagement feature, which is formed as a peripheral channel 632 to receive the peripheral flange 342 of the navigation marker 340. The distal end of the carrier housing 630 includes a plurality of proximally extending arms 638 that are formed in cut-outs and have a threaded exterior portion 639 that is configured to thread the carrier housing 630 into the socket 620, as shown in more detail in FIG. 6B.

FIG. 6B is a cross-sectional view of the embodiment of FIG. 6A, showing the inner threading 629 of the socket 620 that is configured to receive that external thread 539 of the carrier housing 530. Additionally, the structure of the carrier housing 630 is shown to include a continuous ring 635 from which the plurality arms 631 extend proximally, and below which, the cut-outs are formed to include the proximally extending arms 638. In operation, the carrier housing 630, with the navigation marker 340 secured therein, is threaded into the socket 630 such that the threaded exterior portion 639 of the proximally extending arms 638 interfaces with the threads 629 of the socket 620. The carrier housing 630 does not include a driving feature on its bottom distal surface like the carrier housing 530 described above. Instead, the carrier housing 630 can be removed from the socket 620 using a tool that approaches from the proximal side of the frame 310 and extends into the slots between the proximally extending arms 631 to allow threaded removal of the carrier housing, or using a tool that extends from the distal side of the frame 310 and urges the proximally extending arms 638 radially inward to separate the threads 639 formed on the arms 638 from the threads 629 of the socket 620. The latter configuration can allow for a more rapid release of the carrier housing and navigation marker assembly from the socket 620, as it can eliminate the need to back out the threaded engagement between the two components.

Figure 6C:
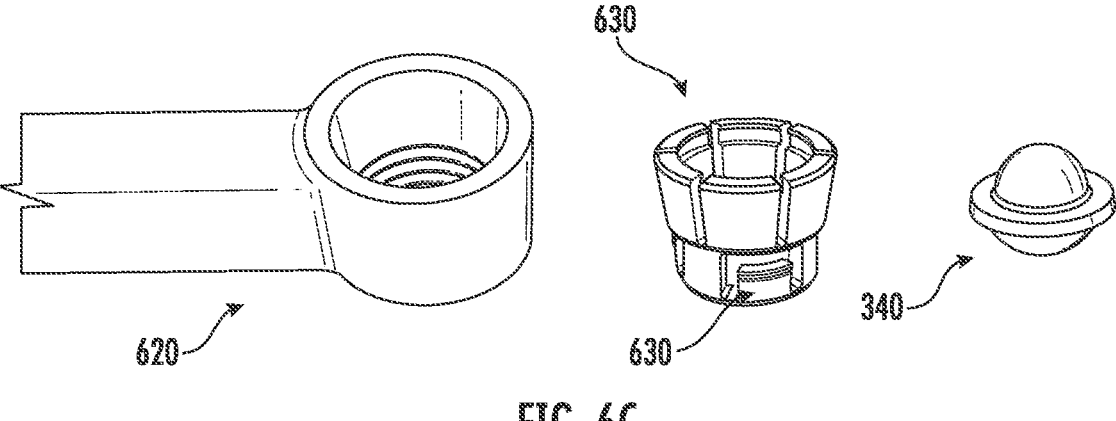
FIG. 6C is a perspective-view photograph of the components of the embodiment of FIG. 6A.
Figure 6D:
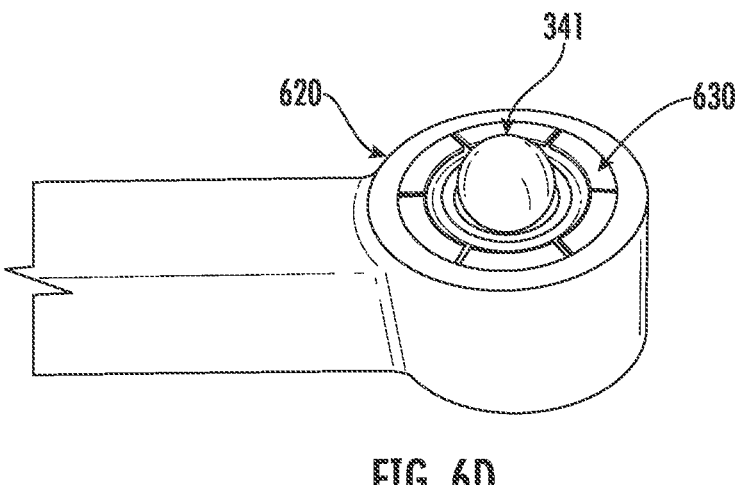
FIG. 6D is a perspective-view photograph of the components of FIG. 6C in an installed configuration.

FIG. 6C is a photograph of the components of the embodiment of FIG. 6A, showing the threaded socket 620, the carrier housing 630, with distal external threads 639 visible, and the loose navigation marker 340. FIG. 6D is a photograph of the components of FIG. 6C in an installed configuration, with the navigation marker 340 disposed in the carrier housing 630, with the arms 631 securing the peripheral flange 342 of the navigation marker 340 and with the carrier housing 630 threaded into the socket 620 of the array 305. In some embodiments, the arms 631 are configured to prevent removal of the navigation marker 340 from the carrier housing 630 when the carrier housing 630 is threaded into the socket 620 due to the arms 631 being inwardly compressed into engagement with the peripheral flange 342 of the navigation marker 340 such that the peripheral channel 632 securely retains the navigation marker 340.

Figures 7A, 7B:
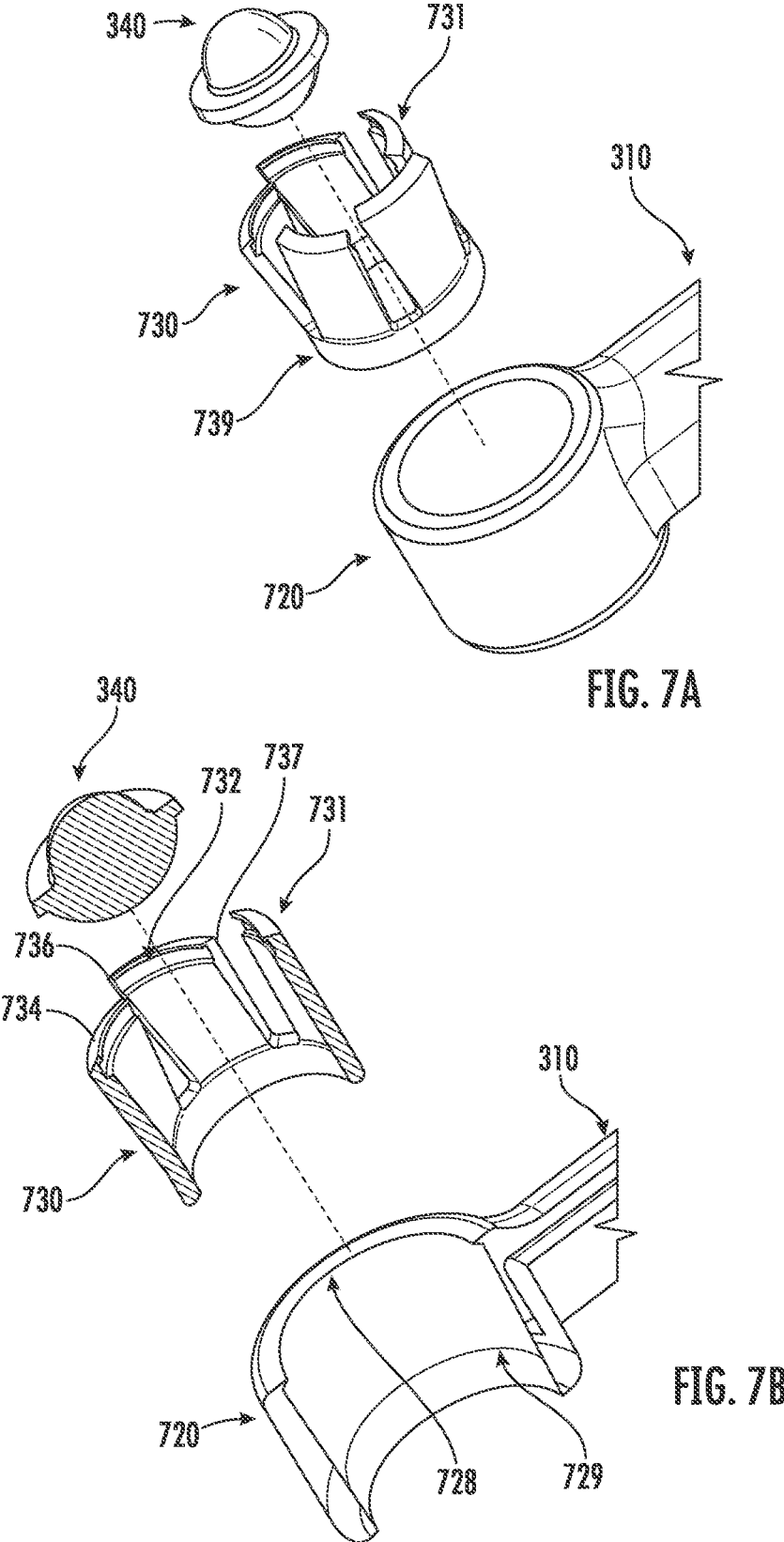
FIG. 7A is an exploded-view illustration of one embodiment of a carrier housing and navigation array coupling socket configured to retain and precisely locate a navigation marker in the coupling socket of the frame of the navigation array.
FIG. 7B is an exploded-cross-sectional view of the embodiment of FIG. 7A.

FIG. 7A is an exploded-view illustration of a yet another embodiment of a carrier housing 730 and coupling socket 720 configured to retain and precisely locate a navigation marker 340 in the coupling socket 720 of the frame 310 of a navigation array 305. The carrier housing 730 incudes a distal continuous ring section 739, from which a plurality of twisted arms 731 extend proximally. The twisted arms 731 together define an opening to receive the navigation marker 340, with each twisted arm 731 having an internal engagement feature, which is formed as a peripheral channel 732 to receive the peripheral flange 342 of the navigation marker 340.

FIG. 7B is a cross-sectional view of the embodiment of FIG. 7A and shows that, in this example, the carrier housing 730 is configured to create an interference fit between the exterior of each arm 731 and the inner surface 729 of the coupling socket 720. Additionally, the proximal edge of the coupling socket 720 includes an inwardly-projecting lip 728 that is configured to retain each arm 731 of the carrier housing 730 when the carrier housing is fully inserted into the coupling socket 720. The carrier housing 730 can include a beveled edge 734 at the outer proximal end of each arm 731 to be engaged by the inwardly-projecting lip 728 in an inserted arrangement. In operation, the twist of each arm 731 defines an outer edge 736 and an inner edge 737 at the proximal end. The twist of each arm 731 creates a condition whereby the peripheral channel 732 at the inner edge 737 is configured to be engaged with the peripheral flange 342 of the navigation marker 340 and the beveled edge 734 at the outer proximal end of each arm 731 is configured to be contacted by the socket 720 when inserted. Moreover, the twist of each arm 731 can be sufficient to require each arm 731 to be deflected in a manner that reverses the twist of each arm 731 when the navigation marker 340 is retained by the arms 731 and the carrier housing 730 is disposed in the socket 720. This installed arrangement is shown more clearly in the photograph of FIG. 7D.

Figure 7C:
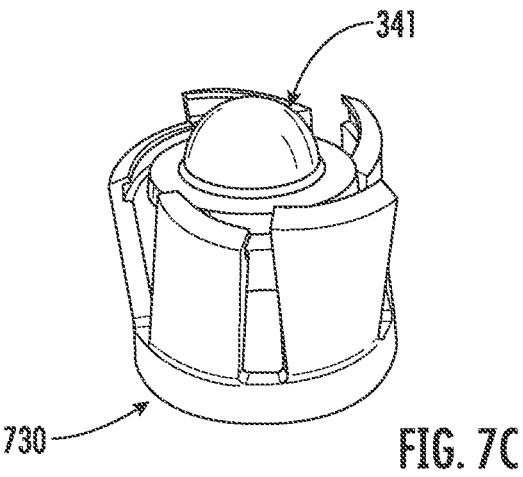
FIG. 7C is a perspective-view photograph of the components of the embodiment of FIG. 7A.
Figure 7D:
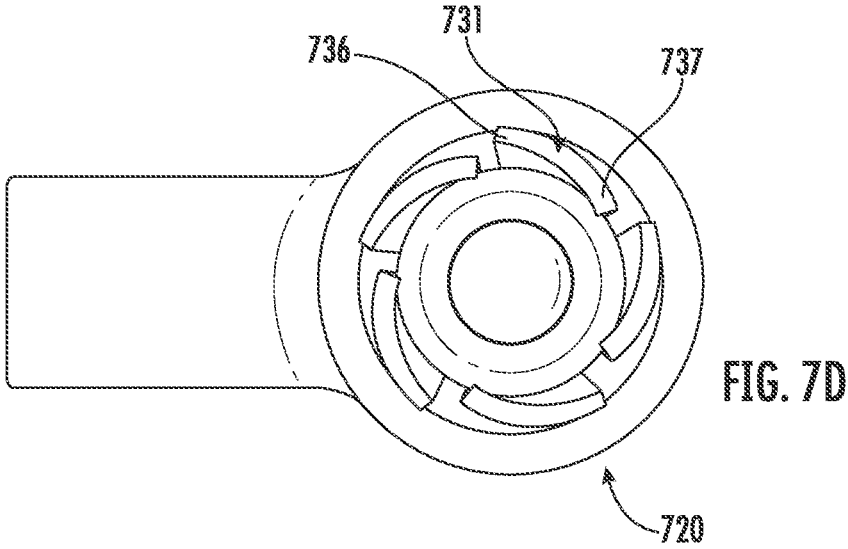
FIG. 7D is a perspective-view photograph of the components of FIG. 7C in an installed configuration.

FIG. 7C is a photograph of the components of the embodiment of FIG. 7A, showing the navigation marker 340 being retained by the arms 731 of the carrier housing 730 prior the carrier housing be disposed in the socket 730 of the array 305. FIG. 7D is a photograph of the components of FIG. 7C in an installed configuration, with each arm 731 having the outer edge 736 in contact with the inner surface of the socket 730 and the inner edge 737 maintaining the retaining-contact with the navigation marker 340. Additionally, in the arrangement of FIG. 7D, the outer edge 736 of each arm 731 has been deflected radically inward by the socket 730, which can move each arm 731 in a manner counter to its twist direction, with the resultant restoring force of the material of the arm 731 serving to maintain the arm's 731 contact with both the socket 730 and the navigation marker 740. As can be seen from the top view of FIG. 7D, the symmetrical opposing forces placed on the navigation marker by the arms 731 can self-center the navigation marker relative to the carrier housing 730 and the carrier housing relative to the socket 720.

Figure 8A:
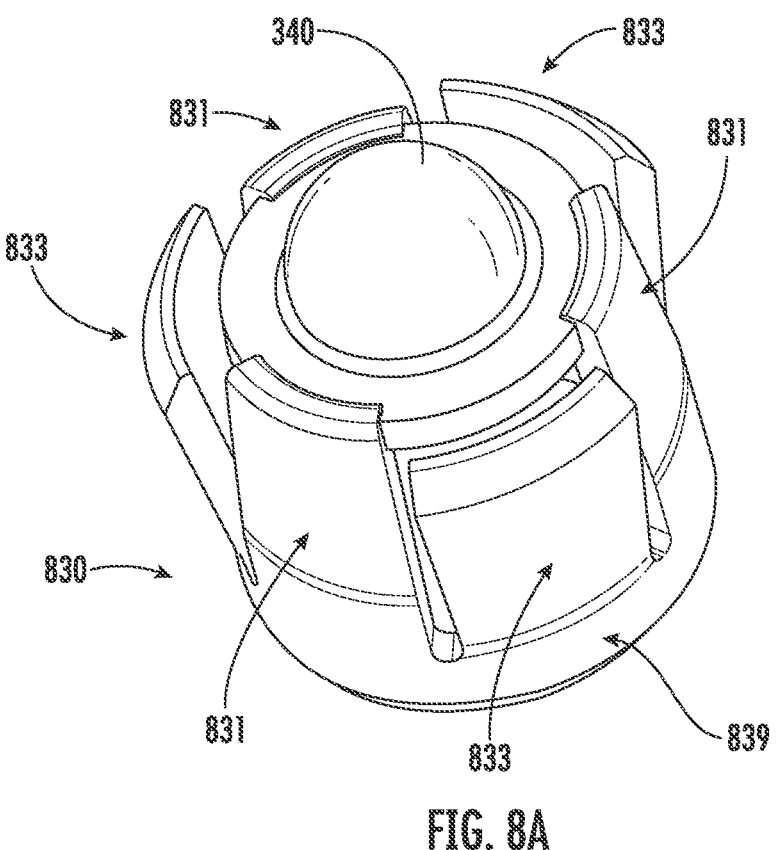
FIG. 8A is an exploded-view illustration of one embodiment of a carrier housing and navigation array coupling socket configured to retain and precisely locate a navigation marker in the coupling socket of the frame of the navigation array.

FIG. 8A is an exploded-view illustration of still another embodiment of a carrier housing 830 and coupling socket (not shown) configured to retain and precisely locate a navigation marker 340 in the coupling socket of the frame 310 of the navigation array 305. The carrier housing 830 includes a distal ring section 839 from which two different sets of arms 831, 833 extend proximally. The first set of arms 831 extend proximally and radially inward and are configured to retain the navigation marker 340 in the carrier housing 340. Each of the first set of arms 831 includes an internal engagement feature, which is formed here as a peripheral channel 832 to receive the peripheral flange 342 of the navigation marker 340. The second set of arms 833 extend proximally and radially outward and are configured to retain the carrier housing 830 in the socket of a navigation array 305. Each of the second set of arms 833 includes beveled edge as shown in more detail in FIG. 8B.

Figure 8B:
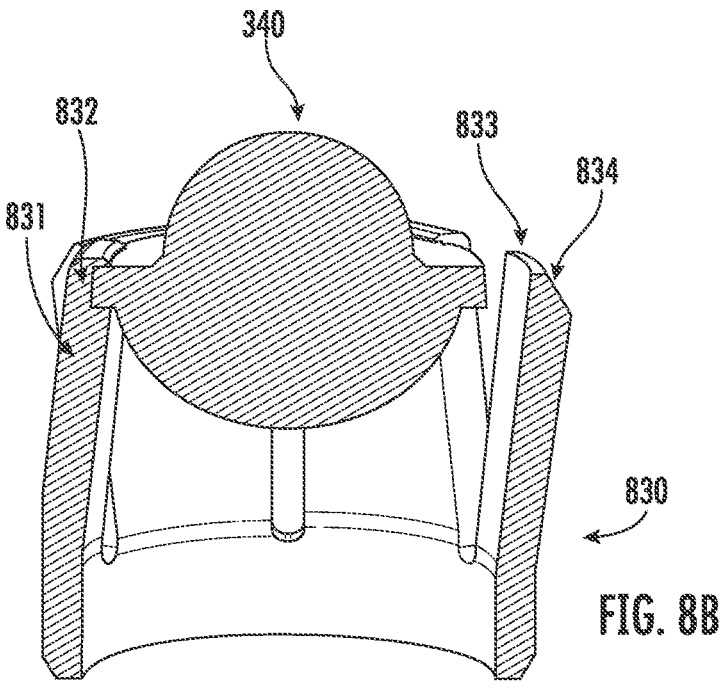
FIG. 8B is a side-cross-sectional view of the embodiment of FIG. 8A.

FIG. 8B is a cross-sectional view of the embodiment of FIG. 8A showing the engagement of the peripheral channel 832 of a first arm 831 with a peripheral flange 342 of the navigation marker 340 and the radially outward resting position of a second arm 833 with a beveled edge 834 at the outer proximal end to be engaged by, for example, an inwardly-projecting lip of a coupling socket of a navigation array 305, as discussed in other embodiments herein. In operation, each of the second set of arms 833 can be deflected radially inwards during insertion of the carrier housing 830 into a coupling socket and the resultant restoring force of each of the second arms 833 in an installed configuration in a coupling socket can center the carrier housing 830 in the coupling socket and serve to further retain the carrier housing 830.

Figure 9A:
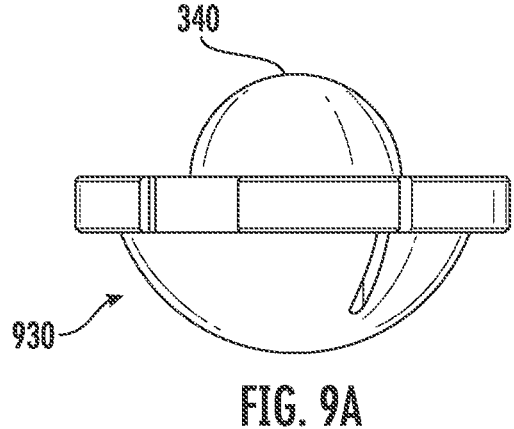
FIG. 9A is a side-view illustration of one embodiment of a carrier housing and navigation marker.
Figure 9B:
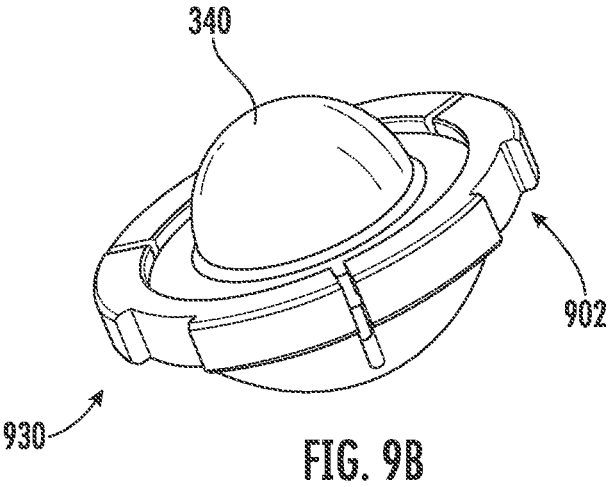
FIG. 9B is a perspective-view illustration of the carrier housing and navigation marker of FIG. 9B.

FIGS. 9A and 9B are illustrations of another embodiment of a navigation marker 340 and carrier housing 930 configured to retain and precisely locate a navigation marker in the coupling socket of the frame of the navigation array. The carrier housing 930 can be configured to fit into a socket (not shown) of corresponding shape formed in a navigation array frame, e.g., a hemispherical socket. Further, recesses 902 or other features formed in the body of the carrier housing 930 can be configured to interface with complementary protrusions or other features formed in the socket of the navigation array frame to ensure a desired fit between the components and to prevent unintended separation of the components.

Figure 10:
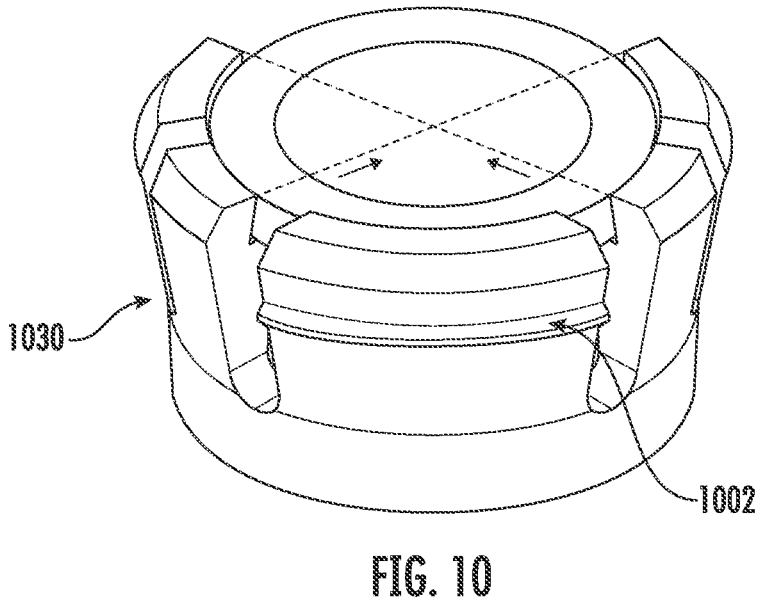
FIG. 10 is a perspective-view illustration of one embodiment of a carrier housing.

FIG. 10 illustrates another embodiment of a carrier housing 1030 that includes one or more retention features 1002 formed on an outer surface thereof. As shown in the figure, each of a plurality of proximally extending arms can include a v-shaped protrusion formed on an outer surface thereof and configured to interface with a complementary groove formed on an inner wall of a socket of a navigation frame (not shown). The retention feature 1002 can be formed on each arm or, as shown in the figure, on alternating arms of the carrier housing 1030. Any of a variety of protrusion profiles or shapes, as well as other features such as recesses, etc., can be utilized in place of the illustrated configuration.

Figure 11:
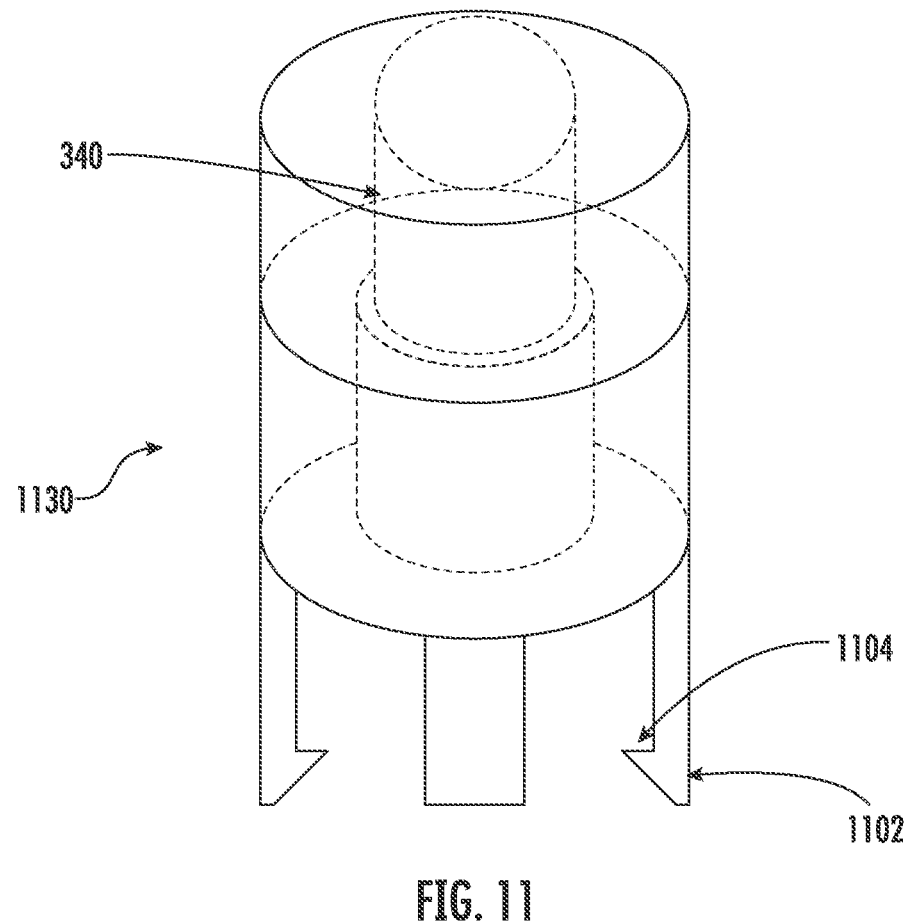
FIG. 11 is a perspective-view illustration of one embodiment of a carrier housing and navigation marker.

FIG. 11 illustrates another embodiment of a carrier housing 1130 that includes a different form of retention features 1102 formed on a distal surface thereof. As shown in the figure, a plurality of distally-extending arms 1102 are formed on a distal/bottom surface of the carrier housing body. Each arm 1102 can include a shelf 1104 formed on a distal portion thereof that can be configured to interface with a corresponding feature formed in the socket of a navigation array frame e.g., a recess, etc. (not shown). The arms 1102 can therefore help position and retain the carrier housing 1130, and thereby the navigation marker 340, relative to a navigation array frame.

Figure 12A:
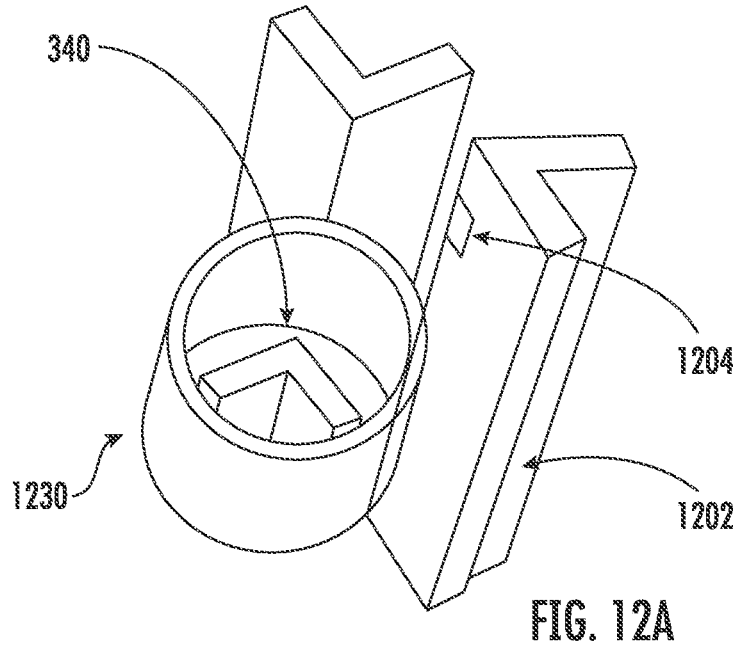
FIG. 12A is a perspective-view illustration of one embodiment of a carrier housing and navigation marker.
Figure 12B:
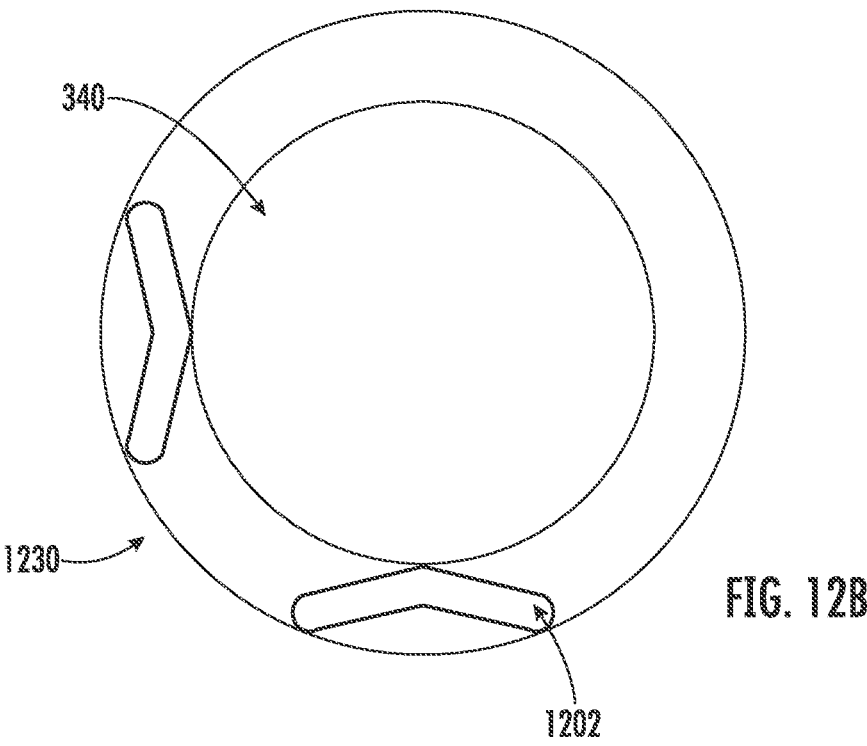
FIG. 12B is a top-view illustration of the carrier housing and navigation marker of FIG. 12A.

FIGS. 12A and 12B illustrate still another embodiment of a carrier housing 1230 that includes proximally-extending arms 1202 in the form of a plurality of v-shaped spring elements. By arranging the v-shaped arms 1202 around the navigation marker 340 in a manner that balances the forces imparted by each arm, the arms can maintain a position of the navigation marker 340 and self-center it relative to the carrier housing 1230 and a socket of a navigation array frame (not shown) in which the carrier housing is disposed. Note that the figures only show a subset of the arms 1202. Further, in some embodiments a plurality of the arms can include a notch 1204 to receive a portion of the navigation marker 340 and aid in seating it securely relative to the carrier housing 1230.

While FIGS. 4A-9B above show a variety of different carrier housings and respective retention arrangements for both the navigation marker 340 in the carrier housing and the carrier housing in the coupling socket of a navigation array frame, other configurations are contemplated and within the scope of this disclosure. For example, while a number of embodiments illustrate the carrier housing having an inner-facing channel or groove to engage with a peripheral edge of the navigation marker 340, other geometries and structural arrangements are contemplated to achieve the same retention along with further securing the navigation marker 340 in the carrier housing when the carrier housing is disposed in a socket of an array 305.

Additionally, while a number of embodiments have shown that utilize a friction/interference fit, lip and edge, and/or a threaded engagement between the carrier housing and the socket in order to retain the carrier housing in the socket, a number of alternative configurations are possible and considered within the scope of this disclosure. For example, the coupling socket can include an inner-facing channel configured to receive a peripheral flange of a carrier housing, as shown, for example, in FIGS. 9A and 9B. In some embodiments, the coupling socket can include a stop, such as a lip or edge, configured to control or limit a maximum insertion depth of the carrier housing. In some embodiments, the outer surface of the carrier housing can include a protruding circumferential edge configured to snap into, or be aligned with, a corresponding peripheral groove in the socket to retain or align the carrier housing the socket. In some embodiments, the carrier housing can include a plurality of distally extending legs or snap features configured to be mated with a corresponding snap feature in the socket, such as a ledge or protrusion. In some embodiments, the carrier housing's snap features can extend radially inward and mate with a corresponding central protrusion formed at a distal end of the socket.

Figures 13A, 13B:
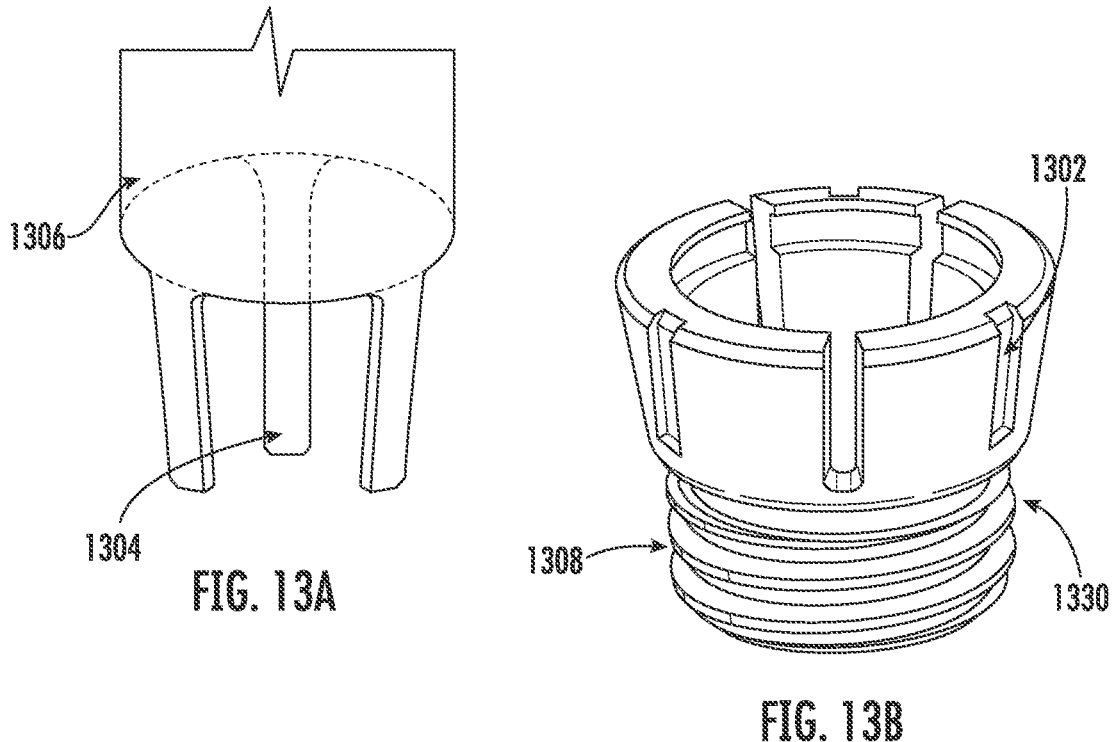
FIG. 13 is a perspective-view illustration of one embodiment of a carrier housing and installation/removal tool.
Figure 14:
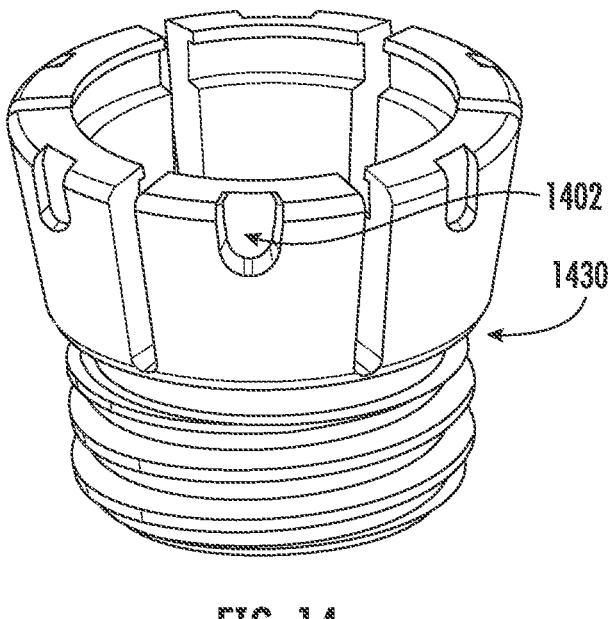
FIG. 14 is a perspective-view illustration of one embodiment of a carrier housing with tool-engagement features.

Further, in some embodiments the carrier housing can include one or more features to interface with an installation/removal tool. FIG. 13, for example, illustrates one embodiment of a carrier housing 1330 that includes slots 1302 formed in an outer surface thereof that are configured to receive distally-extending arms 1304 of an installation/removal tool 1306. The tool 1306 can include a handle or other driving feature that can allow a user to more easily impart force to the carrier housing to, e.g., engage the threads 1308 of the carrier housing with threads formed on an inner surface of a navigation array socket (not shown). A variety of shapes and sizes are possible for the slots 1302. For example, FIG. 14 illustrates another embodiment of a carrier housing 1430 that includes shorter slots 1402 with rounded ends that can interface with complementary-shaped arms of an installation/removal tool (not shown). Any other slot shape or size is also possible, and different surface features besides slots are also possible. In certain embodiments, the installation tool can also include a shoulder or other feature configured to abut with a portion of the navigation array frame when the carrier housing is driven completely into the socket of the frame, thereby preventing over-insertion of the carrier housing.

Figure 15:
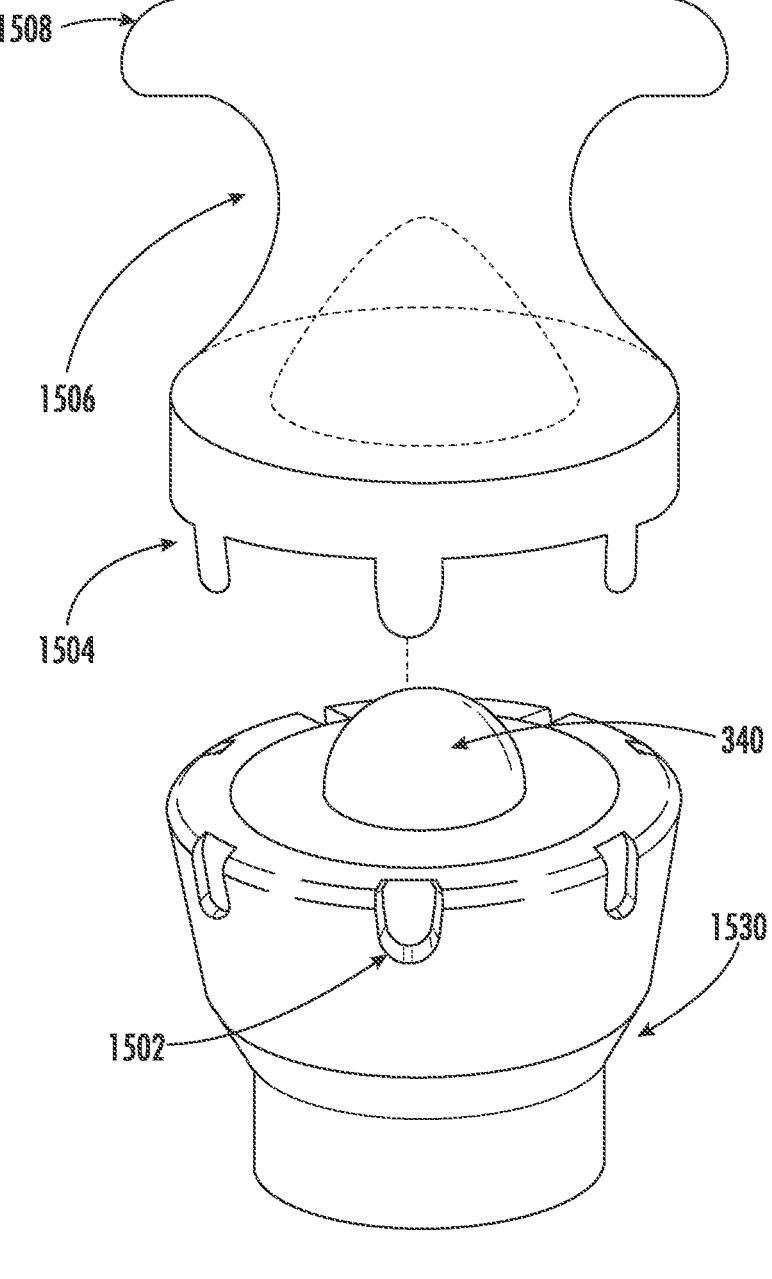
FIG. 15 is a perspective-view illustration of one embodiment of a carrier housing, navigation marker, and installation/removal tool.

FIG. 15 illustrates another embodiment of a carrier housing 1530 coupled to a navigation marker 340, where the carrier housing is configured to interface with an installation/removal tool 1506. In the illustrated embodiment, full-width shallow slots 1502 are formed in a plurality of arms of the carrier housing 1530 and can receive complementary protrusions 1504 on a distal end of the tool 1506. A proximal end of the tool 1506 includes a handle 1508 to allow a user to impart axial and/or rotational force to couple the carrier housing 1530 with a navigation array socket (not shown).

Figure 16:
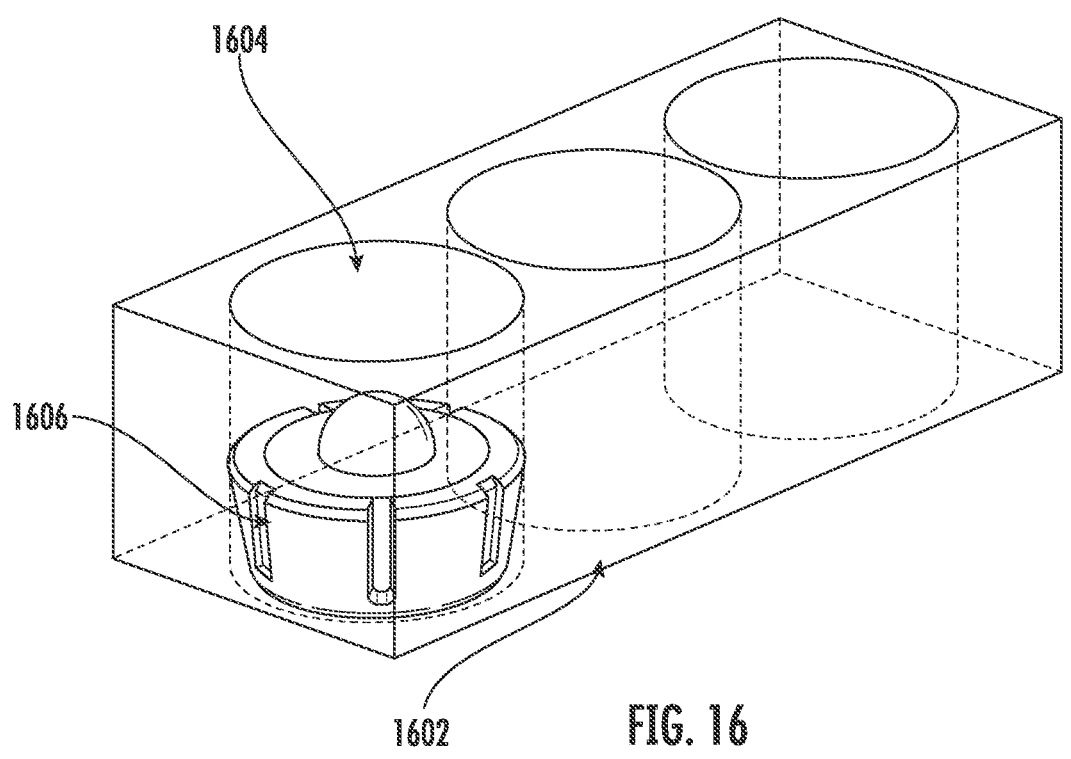
FIG. 16 is a partially-transparent perspective-view illustration of one embodiment of a dispenser for assemblies of a carrier housing and navigation marker.

As mentioned above, in some embodiments assemblies of a carrier housing and navigation marker can be provided in bulk as single use components. In some embodiments, such assemblies can be provided in a dispenser that can be placed in an operating room or surgical prep area so a user can easily dispense one or more new, sterile assemblies to couple to a sterilized single use or reusable navigation array frame. FIG. 16 illustrates one embodiment of such a dispenser 1602 that can include a number of silos 1604 that can each house one or more assemblies 1606 of a carrier housing and a navigation marker according to any of the various embodiments disclosed herein.

Figure 17:
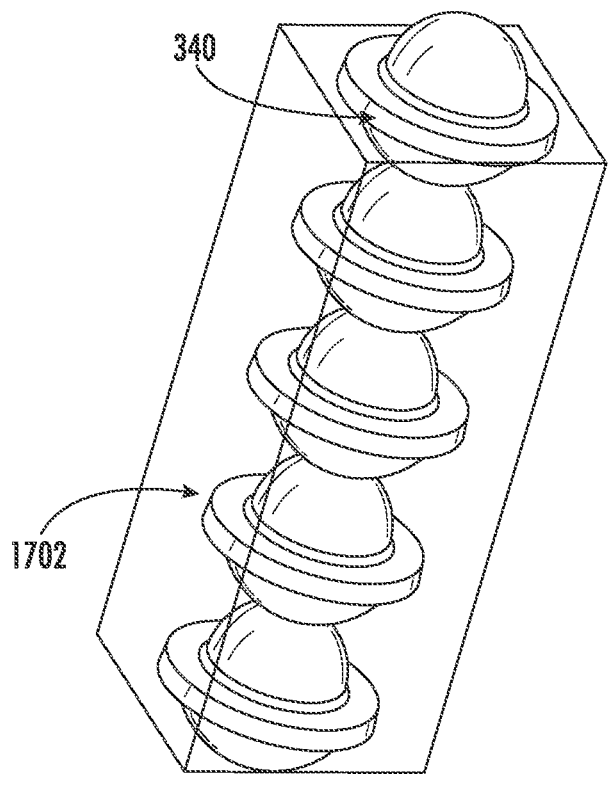
FIG. 17 is a partially-transparent perspective-view illustration of one embodiment of a dispenser for assemblies of a carrier housing and navigation marker.

FIG. 17 illustrates another embodiment of a dispenser 1702 that can include a stacked arrangement of navigation markers 340. Such a dispenser could be combined with a second dispenser (not shown) that could include a stacked arrangement of carrier housings. A user could then dispense a new navigation marker and carrier housing, and then place the marker in the carrier housing before then coupling the assembly to a socket of a navigation array frame.

Figures 18A, 18B:
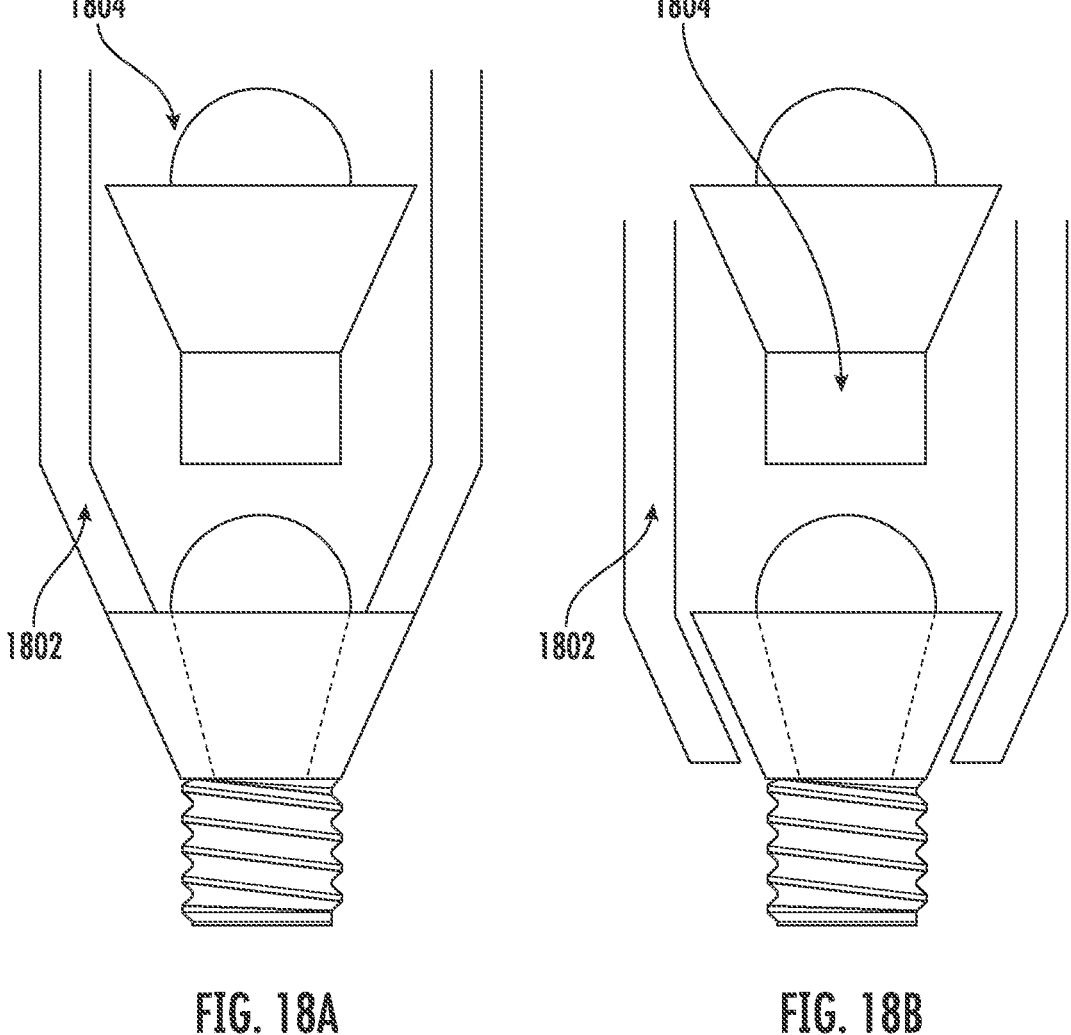
FIG. 18A is a side-cross-sectional view illustration of one embodiment of a dispenser having a plurality of assemblies of a carrier housing and navigation marker.
FIG. 18B is a side cross-sectional view illustration of the dispenser of FIG. 18A with a single assembly of a carrier housing and navigation marker.

FIGS. 18A and 18B illustrate another embodiment of a dispenser 1802 that can house a stacked arrangement of assemblies 1804 of a carrier housing and a navigation marker. FIG. 18A illustrates the dispenser 1804 with a plurality of such assemblies vertically stacked therein and FIG. 18B illustrates the dispenser after a bottom-most assembly in FIG. 18A is dispensed for use.

The devices, systems, and methods disclosed herein can be used in connection with a variety of navigation array frames. In some embodiments, the various embodiments disclosed herein can find utility in connection with flexible navigation arrays that can be configured to couple with rigid frames or instruments to allow modular and flexible array configuration. For example, a rigid frame or instrument including any of a variety of socket configurations can couple with a plurality of navigation markers and carrier housings that are integrated into a flexible navigation array, e.g., connected to one another by a flexible material. The flexible navigation array can be stretched over the rigid frame or instrument and each carrier housing/navigation marker assembly can be disposed in a socket formed in the frame or instrument. Further details on flexible navigation arrays are disclosed in a U.S. patent application entitled "Flexible Navigation Marker Systems and Methods of Use," filed on a same date as this application 20220387112.

The devices, systems, and methods disclosed herein can be used in minimally-invasive surgery and/or open surgery. As noted above, any of a variety of surgical procedures can be performed utilizing the surgical navigation trackers described herein, including various orthopedic procedures, such as knee surgery, spine surgery, shoulder surgery, hip surgery, etc. While the devices and methods disclosed herein are generally described in the context of orthopedic surgery on a human patient, it will be appreciated that the methods and devices disclosed herein can be used in any of a variety of surgical procedures with any human or animal subject, or in non-surgical procedures.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely example embodiments, various other methods that include additional steps or include fewer steps are also within the scope of the present disclosure.

The instruments, devices, and systems disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, silicones, rubbers, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices, systems, and methods disclosed herein can be used in minimally-invasive surgery and/or open surgery. While the devices and methods disclosed herein are generally described in the context of orthopedic surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Reconditioning of a device can utilize a variety of techniques for disassembly, cleaning/replacement, and reassembly. Use of such techniques, and the resulting reconditioned device, are all within the scope of the present disclosure.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

The embodiments of the present disclosure described above are intended to be examples; numerous variations and modifications are possible and within the scope of this disclosure. Accordingly, the disclosure is not to be limited by what has been particularly shown and described. All publications and references cited herein are expressly incorporated by reference in their entirety.

What is claimed is:

1. A coupling system for securing and positioning a navigation marker in a navigation array, the coupling system comprising:
  a reflective navigation marker comprising an at least partially spherical lens, a reflective surface visible through the at least partially spherical lens, and a peripheral flange extending around at least a portion of a periphery of the at least partially spherical lens; and
  a carrier comprising a body configured to be removably disposed in a socket of the navigation array, the carrier body comprising at a distal end, a portion for removably engaging corresponding threaded features of the socket to removably couple the carrier to the navigation array, and, at a proximal end, a plurality of spaced apart arms, the plurality of spaced apart arms defining:
    an open proximal end, an interior void extending distally and inwards from the open proximal end for receiving the reflective navigation marker;
    an inner retaining feature adjacent to the interior void to engage the peripheral flange; and
    an exterior surface configured to engage the socket, wherein rotation of the carrier to engage the carrier body portion with the corresponding threaded features of the socket causes the carrier body to move distally into the socket, the carrier body exterior surface engaging walls of the socket, thereby biasing the plurality of spaced apart arms toward each other to secure and retain the peripheral flange of the reflective navigation marker,
  wherein the at least partially spherical lens is presented at the open proximal end, and wherein the carrier is interposed between the reflective navigation marker and the socket such that the reflective navigation marker does not contact any portion of the navigation array and, wherein, when the carrier body portion is engaged with the corresponding threaded features of the socket, the reflective navigation marker cannot be removed from the carrier, and when the carrier body is removed from the socket, the reflective navigation marker can be removed from the carrier.

2. The coupling system of claim 1, wherein the peripheral flange is hemispherical.

3. The coupling system of claim 1, wherein the interior void of the carrier body is an open cylindrical section.

4. The coupling system of claim 1, wherein the inner retaining feature of the carrier body creates an interference fit with the peripheral flange of the reflective navigation marker.

5. The coupling system of claim 1, wherein the inner retaining feature of the carrier body controls a depth of the reflective navigation marker in the interior void and aligns an axis of the reflective navigation marker with an axis of the carrier.

6. The coupling system of claim 1, wherein the exterior surface of the plurality of spaced apart arms defines a tapered profile.

7. The coupling system of claim 1, wherein the carrier is configured to center the reflective navigation marker in the socket of the navigation array.

8. The coupling system of claim 1, wherein the inner retaining feature is a channel.

9. A coupling system for removably securing and positioning a reflective navigation marker in a navigation array, the coupling system comprising:
  a reflective navigation marker comprising an at least partially spherical lens, a reflective surface visible through the at least partially spherical lens, and a peripheral flange extending around at least a portion of a periphery of the at least partially spherical lens; and
  a carrier configured to be removably disposed in a socket of the navigation array, the carrier comprising a plurality of spaced apart arms defining an interior surface for engaging the peripheral flange and an exterior surface for engaging the socket, wherein, in a mounted position, the carrier is interposed between the reflective navigation marker and the socket such that the reflective navigation marker does not contact any portion of the navigation array and cannot be removed from the carrier, and wherein at least one arm of the plurality of spaced apart arms defines an angle of twist about a distal to proximal longitudinal axis, such that a first proximal edge of the at least one arm of the plurality of spaced apart arms extends further into an interior void defined by the plurality of spaced apart arms than a second proximal edge of the at least one arm of the plurality of spaced apart arms and wherein insertion of the carrier into the socket causes deformation of the at least one arm of the plurality of spaced apart arms and a reduction in the angle of twist to create an interference fit between the peripheral flange and the first proximal edge of the at least one arm of the plurality of spaced apart arms and an interference fit between the socket and the second proximal edge of the at least one arm of the plurality of spaced apart arms.

10. The coupling system of claim 9, wherein at least one arm of the plurality of spaced apart arms defines a curved inner surface and a curved outer surface.

11. The coupling system of claim 9, wherein the exterior surface defines an angled section configured to be engaged by an inwardly extending lip of the socket.

12. The coupling system of claim 9, wherein the plurality of spaced apart arms further comprise a channel adjacent the interior void, wherein the channel engages the peripheral flange to control a depth of the reflective navigation marker in the carrier.

13. A coupling system for securing and positioning a single use navigation marker in a reusable navigation array, the coupling system comprising:
  a single use reflective navigation marker comprising an at least partially spherical reflective navigation lens, a reflective surface visible through the at least partially spherical reflective navigation lens, and a peripheral flange encompassing the at least partially spherical reflective navigation lens; and
  a carrier comprising a plurality of spaced apart arms extending proximally from a distal base, the plurality of spaced apart arms defining an interior void having an open proximal end for receiving the single use reflective navigation marker and an exterior surface configured to engage a socket of the reusable navigation array to removably couple the carrier, and therefore the single use reflective navigation marker, to the reusable navigation array, wherein the carrier is interposed between the single use reflective navigation marker and the socket such that the single use reflective navigation marker does not contact any portion of the reusable navigation array and, wherein, in a first position where the carrier is in the socket, one or more of the plurality of spaced apart arms is biased to engage the single use reflective navigation marker, such that the single use reflective navigation marker cannot be removed from the carrier, and in a second position where the carrier is removed from the socket, the single use reflective navigation marker can be removed from the carrier.

14. The coupling system of claim 13, wherein the plurality of spaced apart arms further comprise a channel adjacent the interior void, wherein the channel engages the peripheral flange, thereby preventing further insertion of the single use reflective navigation marker into the interior void to control a depth of the single use reflective navigation marker in the carrier and align an axis of the single use reflective navigation marker with an axis of the carrier.

15. The coupling system of claim 13, wherein at least one arm of the plurality of spaced apart arms defines an angle of twist about a longitudinal axis, such that a first proximal edge of the at least one arm of the plurality of spaced apart arms extends further into the interior void than a second proximal edge of the at least one arm of the plurality of spaced apart arms, such that insertion of the carrier into the socket causes deformation of the at least one arm of the plurality of spaced apart arms, wherein the first proximal edge of the at least one arm of the plurality of spaced apart arms is biased to create an interference fit with the peripheral flange and wherein the second proximal edge of the at least one arm of the plurality of spaced apart arms creates an interference fit with the socket.

16. The coupling system of claim 13, wherein the distal base further comprises at least one feature for engaging corresponding threaded features of the socket, wherein insertion and rotation of the carrier into the socket causes deformation of the plurality of spaced apart arms, thereby biasing the plurality of spaced apart arms toward each other to secure and retain the peripheral flange.

17. The coupling system of claim 13, wherein at least one arm of the plurality of spaced apart arms is curved proximally and radially inward and at least one arm of the plurality of spaced apart arms is curved proximally and radially outward.

18. The coupling system of claim 17, wherein the at least one arm of the plurality of spaced apart arms that is curved proximally and radially inward further comprises a channel formed on an interior surface to engage the peripheral flange.

19. The coupling system of claim 17, wherein the at least one arm of the plurality of spaced apart arms that is curved proximally and radially outward further comprises a bevel formed on the exterior surface configured to be engaged by an inwardly extending lip of the socket.

20. The coupling system of claim 17, wherein the at least one arm of the plurality of spaced apart arms that is curved proximally and radially outward engages the socket in an interference fit.

* * * * *